(12) United States Patent
Mellem et al.

(10) Patent No.: US 11,676,732 B2
(45) Date of Patent: Jun. 13, 2023

(54) MACHINE LEARNING-BASED DIAGNOSTIC CLASSIFIER

(71) Applicant: BlackThorn Therapeutics, Inc., Brisbane, CA (US)

(72) Inventors: Monika Sharma Mellem, Falls Church, VA (US); Yuelu Liu, South San Francisco, CA (US); Parvez Ahammad, San Jose, CA (US); Humberto Andres Gonzalez Cabezas, Santa Clara, CA (US); William J. Martin, San Francisco, CA (US); Pablo Christian Gersberg, San Francisco, CA (US)

(73) Assignee: NEUMORA THERAPEUTICS, INC., Brisbane, CA (US)

( * ) Notice: Subject to any disclaimer, the term of this patent is extended or adjusted under 35 U.S.C. 154(b) by 18 days.

(21) Appl. No.: 17/446,633

(22) Filed: Sep. 1, 2021

(65) Prior Publication Data
US 2021/0398685 A1 Dec. 23, 2021

Related U.S. Application Data

(63) Continuation of application No. 16/514,879, filed on Jul. 17, 2019, now Pat. No. 11,139,083, which is a
(Continued)

(51) Int. Cl.
*G16H 50/30* (2018.01)
*G16H 50/20* (2018.01)
*G16H 10/60* (2018.01)

(52) U.S. Cl.
CPC ............. *G16H 50/30* (2018.01); *G16H 10/60* (2018.01); *G16H 50/20* (2018.01)

(58) Field of Classification Search
CPC .......... G16H 50/30; G16H 10/60; G16H 50/20
(Continued)

(56) References Cited

U.S. PATENT DOCUMENTS 6,071,236 A * 6/2000 Iliff ....................... G16H 10/20
128/920
2009/0299645 A1 12/2009 Colby et al.
(Continued)

FOREIGN PATENT DOCUMENTS

CN 102858991 A 1/2013
CN 104254863 A 12/2014
(Continued)

OTHER PUBLICATIONS

Extended European Search Report for EP Application No. 19796930. 6, dated Dec. 15, 2021 (9 pages).
(Continued)

*Primary Examiner* — Michael Tomaszewski
(74) *Attorney, Agent, or Firm* — Nixon Peabody LLP

(57) ABSTRACT

Systems and methods for utilizing machine learning to generate a trans-diagnostic classifier that is operative to concurrently diagnose a plurality of different mental health disorders using a single trans-diagnostic questionnaire that includes a plurality of questions (e.g., 17 questions). Machine learning techniques are used to process labeled training data to build statistical models that include trans-diagnostic item-level questions as features to create a screen to classify groups of subjects as either healthy or as possibly having a mental health disorder. A subset of questions is selected from the multiple self-administered mental health questionnaires and used to autonomously screen subjects across multiple mental health disorders without physician involvement, optionally remotely and repeatedly, in a short amount of time.

21 Claims, 12 Drawing Sheets

Related U.S. Application Data continuation of application No. 16/400,312, filed on May 1, 2019.

(60) Provisional application No. 62/665,243, filed on May 1, 2018.

(58) Field of Classification Search
USPC .......................................................... 705/2–3
See application file for complete search history.

(56) References Cited

U.S. PATENT DOCUMENTS

| | | | |
|---|---|---|---|
| 2011/0082712 | A1 | 4/2011 | Eberhardt, III et al. |
| 2014/0243608 | A1 | 8/2014 | Hunt |
| 2014/0276549 | A1 | 9/2014 | Osorio |
| 2015/0288924 | A1 | 10/2015 | Liu et al. |
| 2016/0180038 | A1 | 6/2016 | Clark et al. |
| 2016/0192889 | A1 | 7/2016 | Koutsouleris et al. |
| 2016/0210442 | A1 | 7/2016 | Ethington et al. |
| 2017/0018007 | A1 | 1/2017 | Defrank et al. |
| 2017/0168070 | A1 | 6/2017 | Oberoi et al. |
| 2017/0181668 | A1 | 6/2017 | Abe |
| 2017/0340261 | A1 | 11/2017 | Torres |
| 2018/0116574 | A1 | 5/2018 | Short et al. |
| 2018/0342329 | A1 | 11/2018 | Rufo et al. |
| 2019/0043610 | A1 | 2/2019 | Vaughan |
| 2019/0102511 | A1 | 4/2019 | Murray et al. |
| 2019/0110754 | A1 | 4/2019 | Rao et al. |
| 2019/0117143 | A1 | 4/2019 | Fedor et al. |
| 2019/0230170 | A1 | 7/2019 | Marlin et al. |
| 2019/0239791 | A1* | 8/2019 | Beck ...................... A61B 3/112 |
| 2019/0272889 | A1* | 9/2019 | Murray .................. G16B 20/00 |
| 2019/0341152 | A1 | 11/2019 | Mellem et al. |

FOREIGN PATENT DOCUMENTS

| | | |
|---|---|---|
| CN | 104657929 A | 5/2015 |
| CN | 105247561 A | 1/2016 |
| WO | 2017106770 A1 | 6/2017 |
| WO | 2017210502 A1 | 12/2017 |
| WO | 2018170492 A1 | 9/2018 |
| WO | 2019070721 A1 | 4/2019 |
| WO | 2019070745 A1 | 4/2019 |
| WO | 2019213221 A1 | 11/2019 |

OTHER PUBLICATIONS

International Search Report and Written Opinion of International Searching Authority for Application No. PCT/US2018/054009, dated Feb. 4, 2019 (21 pages).

International Search Report and Written Opinion of International Searching Authority for Application No. PCT/US2019/030149, dated Jul. 17, 2019 (10 pages).

Komorowski, A. et al.; "Association of Protein Distribution and Gene Expression Revealed by PET and Post-Mortem Quantification in the Serotonergic System of the Human Brain"; Cerebral Cortex, vol. 27, No. 1, pp. 117-130; Nov. 30, 2016 (14 pages).

Yan, J. et al.; "Transcriptome-guided amyloid imaging genetic analysis via a novel structured sparse learning algorithm"; Bioinformatics, vol. 30, No. 17, pp. i564-i571; Sep. 1, 2014 (8 pages).

Kessler, R. C. et al., "Short screening scales to monitor population prevalences and trends in non-specific psychological distress," Psychological Medicine, vol. 32, pp. 959-976, Cambridge University Press, 2002 (18 pages).

Kessler, R. C. et al., "Screening for Serious Mental Illness in the General Population," Arch. Gen. Psychiatry, vol. 60, pp. 184-189, Feb. 2003 (6 pages).

Kessler, R. C. et al., "The WHO World Mental Health (WMH) Surveys," Psychiatrie (Stuttg.), 6(1):5-9, Jan. 1, 2009 (6 pages).

White, P. D. et al, "Time to end the distinction between mental and neurological illnesses," BMJ, vol. 344, pp. 26-28 Jun. 16, 2012 (3 pages).

Letham, B. et al., "Interpretable Classifiers Using Rules and Bayesian Analysis: Building a Better Stroke Prediction Model," Annals of Applied Statistics, 9(3):1350-1371, Institute of Mathematical Statistics 2015 (23 pages).

Molnar, C. "Interpretable Machine Learning A Guide for Making Black Box Models Explainable: Chapter 4, Interpretable Models," publication date unknown (82 pages).

Webb, C. et al., "Personalized prediction of antidepressant v. placebo response: evidence from the EMBARC strudy," Psychological Medicine, pp. Jul. 1-10, 2018 (11 pages).

Pampouchidou, A. et al., "Depression Assessment by Fusin Hih and Low Level Features from Audio, Video, and Text," AVEC 2016, Oct. 16, 2016 (8 pages).

Valstar, M. et al. "AVEC 2016—Depression, Mood, and Emotional Recognition Workshop and Challenge," Proceedings for the 6th International Conference on Multimedia (ACM MM), pp. 3-10 Amsterdam, Netherlands, Oct. 2016 (9 pages).

* cited by examiner

MACHINE LEARNING-BASED DIAGNOSTIC CLASSIFIER

CROSS REFERENCE TO RELATED APPLICATIONS

This application is a continuation of U.S. application Ser. No. 16/514,879, filed on Jul. 17, 2019, which is a continuation of U.S. application Ser. No. 16/400,312, filed on May 1, 2019, which claims priority to and the benefit of U.S. Provisional Patent Application No. 62/665,243, filed on May 1, 2018, each of which is hereby incorporated by reference herein in its entirety.

FIELD

The present disclosure generally relates to medical diagnostic tools, and more particularly, to systems and methods for machine learning-based mental health diagnostic tools.

BACKGROUND

Mental health screening and diagnosis requires a time-consuming interview between patients and highly-trained specialists within a clinic. Currently available remotely-administered self-assessments tend to be based on discrete diagnostic categories that may fail to reveal trans-diagnostic or sub-clinical behavioral changes that warrant intervention.

SUMMARY

The various examples of the present disclosure are directed towards systems and methods for screening the mental health of patients. In a first embodiment, an exemplary system includes a display, a microphone, a camera, a memory, and a control system. The camera is positioned to capture an image in front of the display and configured to output video data. The memory contains machine readable medium comprising machine executable code and has stored instructions for performing a method of evaluating the mental health of a user. The control system is coupled to the memory, includes one or more processors, and executes the machine executable code. This causes the control system to perform the following series of steps.

The control system executes a test application, upon receiving, from the user interface, an indication to initiate a test. The control system terminates the test application upon receiving an indication to stop the test. The test application includes (1) displaying, on the display, a series of questions from mental health questionnaires comprising text and answers for each question, (2) displaying, on the display, live video data recorded by the camera, (3) recording, by the camera, a set of test video data, (4) recording, by the microphone, a set of test audio data, (5) receiving, though the user interface, an answer for each of the series of questions to yield a selection of answers, and (6) processing, using a machine learning model, the selection of answers, the set of test video data, and the set of audio data to output a mental health indication of the user.

In some examples, the indication to stop the test application is a determination, by the control system, that a user face is not within an image captured by the camera.

In some examples, recording, by the microphone, includes initiating the recording upon determining, by the control system, that the user is speaking.

In some examples, the control system is configured to perform additional steps, including receiving the set of test video data and the set of test audio data. The received set of test video data is preprocessed to identify a plurality of video segments, each video segment corresponding to one question in the series of questions and comprising a time window. The received set of test audio data is preprocessed to identify a plurality of audio segments, each audio segment corresponding to one question in the series of questions and comprising a time window.

In some examples, the plurality of audio segments and the plurality of video segments are preprocessed to identify overlapping time windows. The control system outputs a set of integrated audio and video segments based on the identified overlapping time windows.

In some examples, the machine learning model is any of a generalized linear model, a regression model, a logistical regression model, and/or a supervised machine learning classification model.

In some examples, the machine learning model is a generalized linear model generated by performing a series of steps. The steps provide for receiving labeled training data for a plurality of individuals. The labeled training data includes (1) indications whether each of the plurality of individuals has one or more mental health disorders, (2) audio and video data recorded for each of the plurality of individuals recording during a training test, and (3) a selection of answers to the questionnaires from each of the plurality of individuals. The steps then provide for determining a plurality of features from the labeled training data and training an initial machine learning model in a supervised manner, based on the plurality of features. The steps then provide for extracting importance measures for each of the plurality of features, based on the training of the initial machine learning model. A plurality of subset machine learning models is then generated based on the extracted importance measures for the plurality of features. A classification performance of the generated plurality of subset machine learning models is then evaluated; and based on the evaluation, at least one of the subset machine learning models is selected as the generalized linear model.

In some examples, the mental health indication identifies a likelihood of the user having one of a plurality of mental health disorders, including a neuropsychiatric disorder, schizophrenia, and/or a bipolar disorder. In some examples, the mental health indication identifies whether the user is a patient or a healthy control.

A second embodiment of the present disclosure provides a system, including a display, a microphone, a camera, a memory, and a control system. The camera is positioned to capture an image in front of the display and configured to output video data. The memory contains machine readable medium comprising machine executable code and has stored instructions for performing a method of evaluating the mental health of a user. The control system is coupled to the memory, includes one or more processors, and executes the machine executable code. This causes the control system to perform the following series of steps.

The control system executes a test application, upon receiving, from the user interface, an indication to initiate a test. The control system terminates the test application upon receiving an indication to stop the test. The test application provides for (1) displaying text on the display for the user to read, (2) recording, by the camera, a set of test video data during the test, (3) displaying, on the display, a window displaying live video data recorded by the camera, (4) continually processing the set of test video data during the test, (5) recording, by the microphone, a set of test audio data during the test, and (6) processing the set of test audio data and test video data to identify audio and video features and storing the audio and video features in the memory. The continual processing step provides for identifying a face of the user, and determining whether all of a plurality of pixels of the face are within a frame. If the face is outside the frame, the processing step provides for stopping the test.

In some examples, the displayed text comprises a series of questions from mental health questionnaires including text and answers for each question.

In some examples, each of the audio and video features correspond to a question in the series of questions.

Additional examples of the second embodiment are provided for as with respect to the first embodiment.

A third embodiment of the present disclosure provides a system for screening the mental health of patients, the system includes a memory and a control system. The memory contains machine readable medium comprising machine executable code and has stored instructions for performing a method of evaluating the mental health of a user. The control system is coupled to the memory, includes one or more processors, and executes the machine executable code. This causes the control system to (1) receive a set of answer data representing answers from a user to a series of questions from mental health questionnaires, (2) receive a set of test video data recorded during a test representing the face of the user while the user is reading text, (3) process the set of test video data to output a set of video features, (4) receive a set of test audio data recorded during the test representing the voice of the user while the user is reading text, (5) process the set of audio data to output a set of audio features, and (6) process, using a machine learning model, the set of answer data, the set of video features, and the set of audio features to output an indication of the mental health of the user. In some examples, the machine learning model is any of: a generalized linear model, a regression model, a logistical regression model, and/or a supervised machine learning classification model. Additional embodiments of the third embodiment are as provided for above with respect to the first and second embodiments.

A fourth embodiment of the present disclosure provides machine learning training system. The system includes at least one non-transitory processor-readable storage medium and at least one processor. The storage medium stores at least one of processor-executable instructions or data. The processor is communicatively coupled to the at least one non-transitory processor-readable storage medium. In operation, the at least one processor is configured to receive labeled training data. The training data includes data for a plurality of individuals that indicates whether each of the plurality of individuals has one or more of a plurality of mental health disorders. The training data additionally includes (1) answers to mental health questionnaires, and (2) video data and audio data. The mental health questionnaires were administered to the plurality of individuals. The video data and audio data were recorded while each of the plurality of individuals read text from a digital display. The video data is processed to identify portions of the video data comprising the face of the individual, and the audio data is processed to identify sounds representing the voice of the individual. The processor is further configured to process the answers, the audio data, and the video data to output a plurality of features. The processor then trains an initial machine learning model in a supervised manner based on the received training data. The processor then extracts an importance measure for each of the plurality of features from the trained initial machine learning model. The processor then generates a plurality of subset machine learning models based on the extracted importance measures for the plurality of features. The processor then evaluates a classification performance of the generated plurality of subset machine learning models. The processor then selects at least one of the plurality of subset machine learning models as a diagnostic classifier. The processor then stores the features of the diagnostic classifier in the at least one non-transitory processor-readable storage medium for subsequent use as a screening tool.

In some examples, the selected subset machine learning model includes a portion of the plurality of features, the portion selected from features having an importance measure above a threshold value.

In some examples, at least twenty features of the plurality of features have an importance measure above the threshold value, and the portion includes at least ten features and less than twenty features.

In some examples, each of the subset machine learning models includes a different selection of the portion of the plurality of features.

In some examples, the diagnostic classifier outputs a mental health indication identifying an individual as healthy or as having a general mental health issue.

In some examples, the diagnostic classifier outputs a mental health indication identifying an individual as healthy or as having a specific mental health issue.

In some examples, the diagnostic classifier outputs a mental health indication identifying an individual as having either a first specific mental health disorder or a second specific mental health disorder.

In some examples, the diagnostic classifier outputs a mental health indication identifying a risk of developing a mental health disorder for an individual.

In some examples, the labeled training data further includes, for each individual in the plurality of individuals, an indication of at least one of the following: whether the individual is healthy, whether the individual has a general mental health issue, whether the individual has one or more specific mental health disorders, whether the individual is at risk of developing a general mental health issue, and/or whether the individual is at risk of developing one or more specific mental health disorders.

In some examples, training the initial machine learning model includes using k-fold cross validation with logistic regression.

In some examples, each of the subset machine learning models includes a different combination of the plurality of features.

In some examples, the labeled training data includes at least one of functional measurement data or physiological measurement data.

In some examples, the fourth embodiment provides for using the features of the diagnostic classifier as a screening tool to assess at least one of intermediate or end-point outcomes in at least one clinical trial testing for treatment responses.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
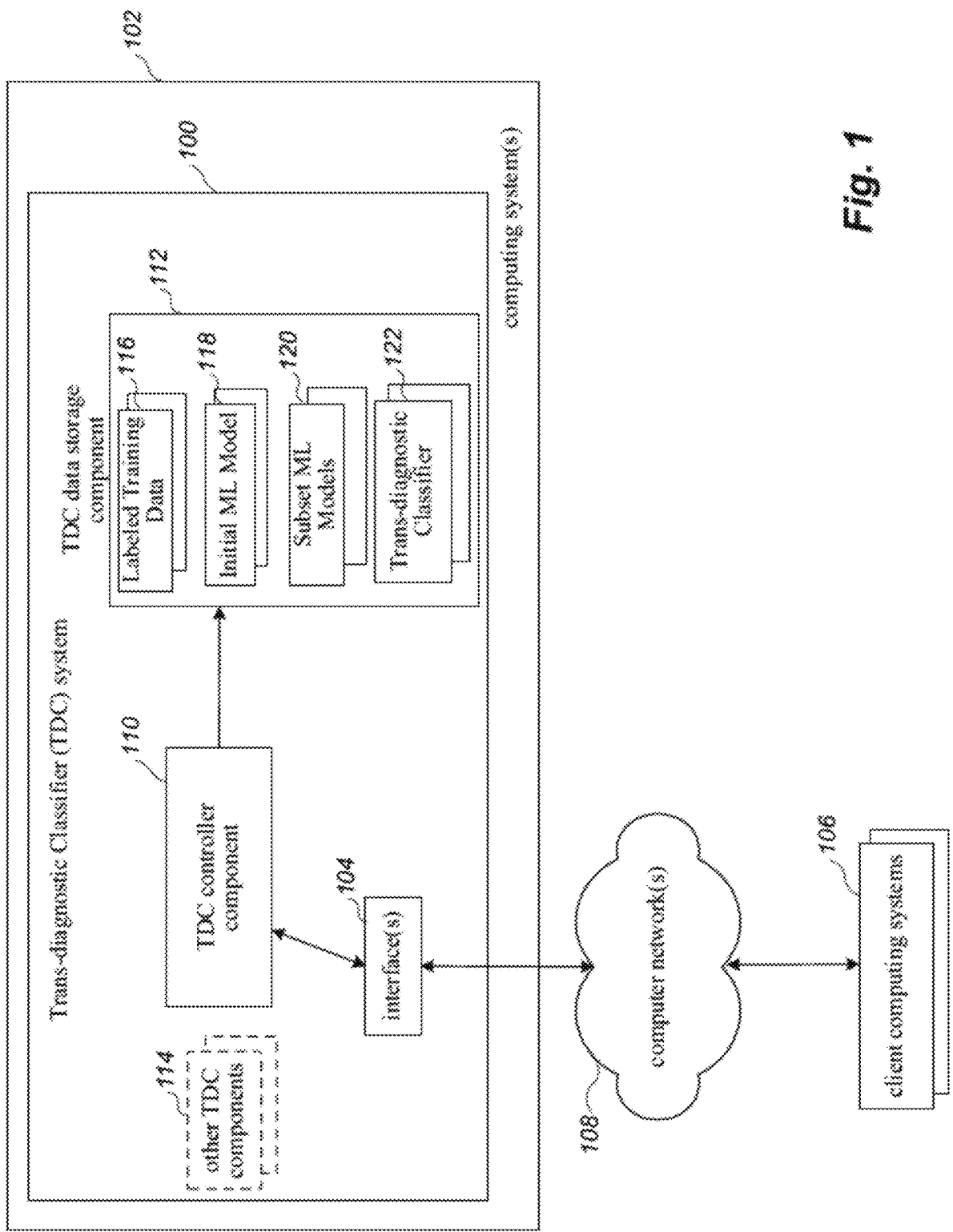
FIG. 1 is a network diagram illustrating an example environment in which a system for training and implementing a machine learning-based trans-diagnostic classifier may be configured, initiated and operated, according to one non-limiting illustrated implementation of the present disclosure.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

This specification describes systems and methods of screening people for mental health disorders by using a machine learning approach to select the most informative questions from a broad set of questionnaires for assessing those disorders. These screens are fast, highly-accurate, and rely only on self-reporting by any individual (they do not need to be administered by a mental health professional). Several screens can be created based on the main goal of the screen, such as: 1) a trans-diagnostic screen (to determine if individual is healthy or has a general mental health issue), 2) a specific-disorder screen (to determine if individual is healthy or has a specific mental health disorder like schizophrenia or ADHD), or 3) a differential-diagnosis screen (to determine if individual has one specific mental health disorder or another specific mental health disorder like schizophrenia rather than ADHD). This approach is not limited to predicting only a subset of specific mental health disorders, as it may be applied to predicting mental health issues, symptoms, or behavioral dimensions in mental health or other disorders (e.g., depression in Parkinson's disease, psychosis in epilepsy, dementia in multiple sclerosis (White et al., 2012)). This approach is also not limited to prediction of mental health problems only using questions/questionnaires as input features, as functional (e.g., smartphone user interactions) or physiological types of measurements (e.g., magnetic resonance imaging, electroencephalography, magnetoencephalography, electrocorticography, positron emission tomography, single-photon emission computed tomography) can also provide an informative set of predictive features to select from for efficient and accurate mental health screening.

This approach outperforms other trans-diagnostic screens based only on a single questionnaire (e.g., Kessler et al., 2002; Kessler et al., 2003) which highlights the advantage of taking the novel approach of combining and selecting a subset of questions from across multiple questionnaires using a machine learning approach. Such an approach may also help identify individuals who may not have a mental health disorder but may be at risk at developing one (e.g., by identifying misclassifications of the model and building additional models to label them as a separate group of at-risk individuals).

As these screens are quick and rely on self-reported answers, this set of screens could be administered from a phone, tablet, or computer app (e.g., mobile app, web browser app), with the collected data processed on the local device or in a cloud-computing environment, and transmitted with the individual's consent to a primary care physician or a mental health professional.

There is a myriad of applications that may use these screens. The following lists several non-limiting examples of applications in which the screens of the present disclosure may be used. The screens can be used by any individual to assess if they may have a mental health disorder. The screens can be used to estimate incidence and prevalence of mental health issues in a given population (e.g., state, national, homeless, military, schools, ethnic, etc.). The screens can be used to assess both intermediate and end-point outcomes in clinical trials testing for treatment responses. The screens can be used as a primary care screening tool for patients with expected mental health issues to reduce inefficient and unnecessary referrals. The screens can be used to quickly triage patients suspected of mental health issues in emergency department settings. The screens can be used to check the likelihood of a self-reported disorder by an individual enrolled in a study recruiting individuals with mental health disorders but not able to have a physician assessment of the disorder. The screens can be used in the workplace as it has been found that identifying and treating mental illness is cheaper than lost productivity to companies (Kessler et al., 2009).

A machine learning system may be summarized as including at least one non-transitory processor-readable storage medium that stores at least one of processor-executable instructions or data; and at least one processor communicatively coupled to the at least one non-transitory processor-readable storage medium, in operation, the at least one processor: receives labeled training data that includes data for a plurality of individuals that indicates whether each of the individuals has one or more of a plurality of mental health disorders, the labeled training data further including item-level responses of at least some of the individuals to multiple self-administered mental health questionnaires that each comprise one or more features; trains an initial machine learning model in a supervised manner based at least in part on the received training data; extracts an importance measure for each of the plurality of features in the multiple self-administered mental health questionnaires from the trained initial machine learning model; generates a plurality of subset machine learning models based at least in part on the extracted importance measures for the plurality of features; evaluates the classification performance of the generated plurality of subset machine learning models; selects at least one of the subset machine learning models as a diagnostic classifier; and stores the features of the diagnostic classifier in the at least one non-transitory processor-readable storage medium for subsequent use as a screening tool. The selected subset machine learning model may include M of the most important N features as determined by the importance measures, wherein M is an integer between 10 and 20 and N is an integer greater than 20. The diagnostic classifier may be operative to determine whether an individual has one of a plurality of mental health disorders. The selected subset machine learning model may include at least a subset of the following features: "I like to please other people as much as I can"; "There are often times when I am so restless that it is impossible for me to sit still"; "My mood often changes, from happiness to sadness, without my knowing why"; "Although there are things that I enjoy doing by myself, I usually seem to have more fun when I do things with other people"; "I am more sentimental than most people"; "I love to excel at everything I do"; "People consider me a rather freewheeling and spontaneous person"; "I feel that I never really get all that I need from people"; "In unfamiliar surroundings, I am often so assertive and sociable that I surprise myself"; "I like to think about things for a long time before I make a decision"; "Sometimes ideas and insights come to me so fast that I cannot express them all"; "I have many hobbies"; "I like to keep my problems to myself"; "It is difficult for me to keep the same interests for a long time because my attention often shifts to something else"; "How often do you have trouble wrapping up the final details of a project, once the challenging parts have been done"; "I like to go slow in starting work, even if it is easy to do"; and "Usually I am more worried than most people that something might go wrong in the future." In operation, the at least one processor may train the initial machine learning model using k-fold cross validation with logistic regression. Each of the subset machine learning models may include a different combination of the features of the initial machine learning model. Each of the subset machine learning models may include a different number of the most important features of the initial machine learning model determined by the importance measures. As would be readily understood by one skilled in the art, variations of these questions can be used in the disclosed systems and methods as well. In various examples of the present disclosure, some additional questions can be used, replacement/alternate questions can be used, or some of the questions can be omitted.

One or more implementations of the present disclosure are directed to systems and methods for utilizing machine learning to generate a trans-diagnostic classifier that is operative to concurrently diagnose a plurality of different mental health disorders using a single trans-diagnostic questionnaire that includes a plurality of questions (e.g., 17 questions), also referred to herein as features. Generally, the inventors of the present disclosure have implemented machine learning techniques to develop a quick, trans-diagnostic, self-administered mental health screen, which is automatically scored, to overcome at least some of the barriers noted above. It is noted that although the examples discussed below include questions/questionnaires as input features for explanatory purposes, it should be appreciated that the systems and methods disclosed herein are not limited to prediction of mental health problems only using questions/questionnaires as input features, as functional (e.g., smartphone user interactions) or physiological types of measurements (e.g., magnetic resonance imaging, electroencephalography, magnetoencephalography, electrocorticography, positron emission tomography, single-photon emission computed tomography) can also provide an informative set of predictive features to select from for efficient and accurate mental health screening. Further, the implementations discussed herein may be used to provide a trans-diagnostic screen, a specific-disorder screen, a differential-diagnosis screen, or other types of screens.

As discussed further below, machine learning techniques may be used to process labeled training data to build statistical models that include trans-diagnostic item-level questions as features to create a screen to classify groups of subjects as either healthy or as possibly having a mental health disorder. The labeled training data may include data for a plurality of individuals that indicates whether each of the individuals has one or more of a plurality of disorders, such as, but not limited to, schizophrenia, bipolar disorder, or attention deficit and hyperactivity disorder (ADHD). For each of the individuals, the labeled training data also includes item-level responses to multiple self-administered mental health questionnaires (e.g., five questionnaires, 10 questionnaires, 20 questionnaires).

Using machine learning techniques, a subset of the questions, e.g., 15-20 questions out of more than 20 questions (e.g., 200 questions, 600 questions), from the multiple self-administered mental health questionnaires may be selected and used to autonomously screen subjects across multiple mental health disorders without physician involvement, optionally remotely and repeatedly, in a short amount of time (e.g., less than 5 minutes). The various features of the implementations of the present disclosure are discussed further below with reference to the figures.

FIG. 1 is a network diagram illustrating an example environment in which a system for generating and implementing a trans-diagnostic classifier (TDC) system 100 may be configured and initiated. In particular, an embodiment of the TDC system 100 is shown executing on one or more computing systems 102, including in the illustrated embodiment to operate in an online manner and provide one or more interfaces 104 (e.g., graphical user interface (GUI), applications programming interfaces (API)) to enable one or more remote users of client computing systems 106 to interact over one or more intervening computer networks 108 with the TDC system 100 to generate, modify, and use one or more trans-diagnostic classifiers.

Using client computing systems 106, one or more users (e.g., researchers, physicians, patients) may interact over the computer network 108 with the TDC system 100 to generate a TDC and to use a generated TDC to screen for a plurality of mental health disorders. In at least some implementations, one or more systems may be used to generate a classifier, and one or more different systems may be used to implement the classifier as a screening tool. The TDC system 100 may include a TDC controller component 110 (e.g., one or more processors), a TDC data storage component 112 (e.g., one or more non-transitory processor-readable storage media), the interfaces 104, and other TDC components 114 (e.g., processors, data storage, wired/wireless interfaces, input/output devices). In the illustrated example, the TDC data storage component 112 stores labeled training data 116, one or more initial machine learning models 118, one or more subset machine learning models 120, and one or more output trans-diagnostic classifiers 122 that may be used to screen subjects for a plurality of mental health disorders. Each of these components is discussed below.

The network 108 may, for example, be a publicly accessible network of linked networks, possibly operated by various distinct parties, such as the Internet, with the TDC system 100 available to any users or only certain users over the network 108. In other embodiments, the network 108 may be a private network, such as, for example, a corporate or university network that is wholly or partially inaccessible to non-privileged users. In still other embodiments, the network 108 may include one or more private networks with access to and/or from the Internet. Thus, while the TDC system 100 in the illustrated embodiment is implemented in an online manner to support various users over the one or more computer networks 108, in other embodiments a copy of the TDC system 100 may instead be implemented in other manners, such as to support a single user or a group of related users (e.g., a company or other organization), such as if the one or more computer networks 108 are instead an internal computer network of the company or other organization, and with such a copy of the TDC system optionally not being available to other users external to the company or other organizations. The online version of the TDC system 100 and/or local copy version of the TDC system may in some embodiments and situations operate in a fee-based manner, such that the one or more users provide various fees to use various operations of the TDC system, such as to use the TDC system 100 to screen one or more individuals for mental health disorders. In addition, the TDC system 100, and/or each of its components, may include software instructions that execute on one or more computing systems (not shown) by one or more processors (not shown), such as to configure those processors and computing systems to operate as specialized machines with respect to performing their programmed functionality.

Figure 2:
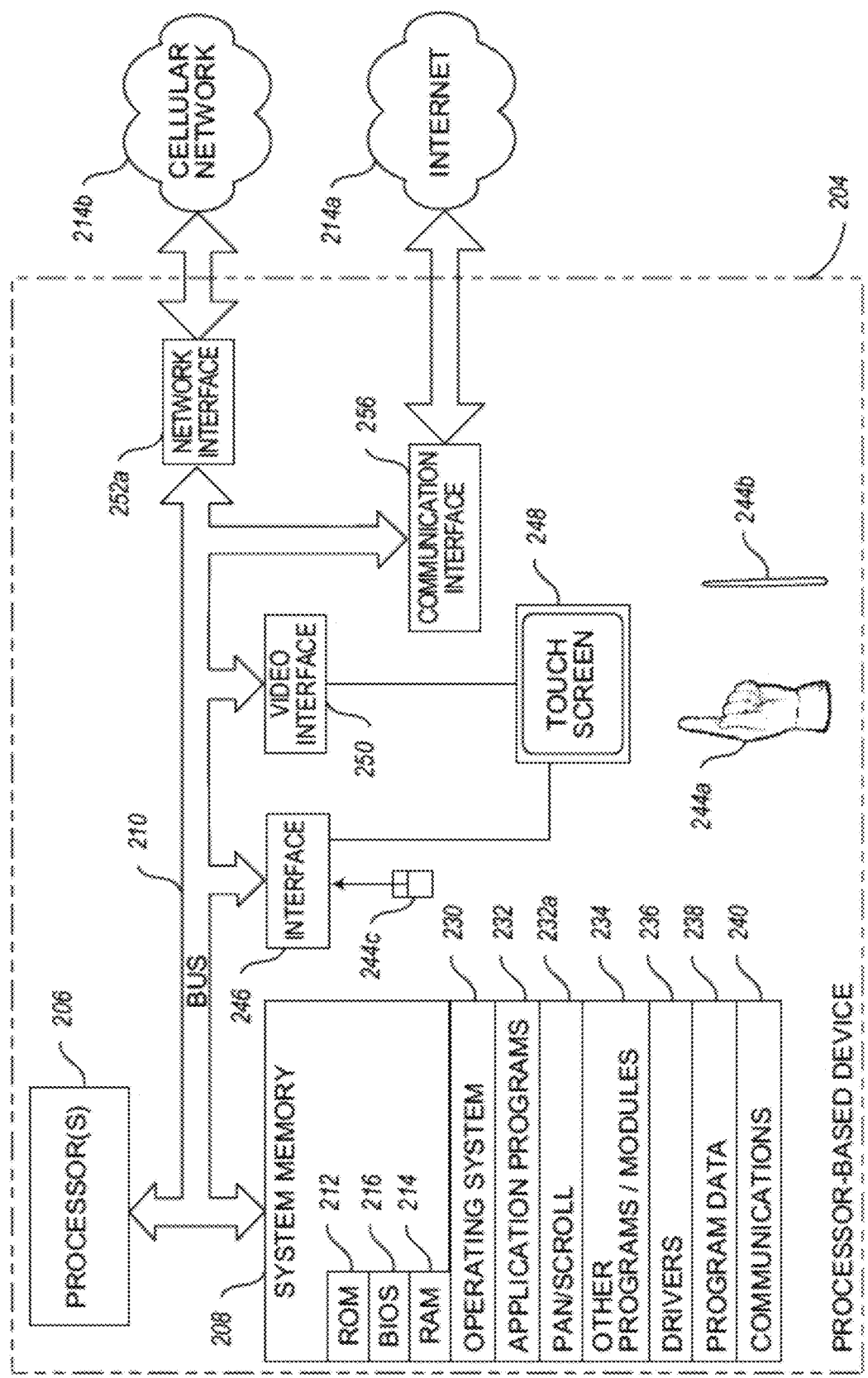
FIG. 2 is a block diagram of an example computing system suitable for executing an embodiment of a machine learning-based trans-diagnostic classifier in configured manners.

FIG. 2 shows an example processor-based device 204 suitable for implementing various embodiments described herein. For example, the processor-based device 204 may be representative of the computing system 102 or one of the client computing systems 106 of FIG. 1. Although not required, some portion of the embodiments will be described in the general context of processor-executable instructions or logic, such as program application modules, objects, or macros being executed by one or more processors. Those skilled in the relevant art will appreciate that the described embodiments, as well as other embodiments, can be practiced with various processor-based system configurations, including handheld devices, such as smartphones and tablet computers, wearable devices, multiprocessor systems, microprocessor-based or programmable consumer electronics, personal computers ("PCs"), network PCs, minicomputers, mainframe computers, and the like.

The processor-based device 204 may, for example, take the form of a server computer, cloud-based computing system, desktop computer, smartphone or tablet computer, which includes one or more processors 206, a system memory 208 and a system bus 210 that couples various system components including the system memory 208 to the processor(s) 206. The processor-based device 204 will at times be referred to in the singular herein, but this is not intended to limit the embodiments to a single system, since in certain embodiments, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, 68xxx series microprocessors from Motorola Corporation.

The processor(s) 206 may be any logic processing unit, such as one or more central processing units (CPUs), microprocessors, digital signal processors (DSPs), application-specific integrated circuits (ASICs), field programmable gate arrays (FPGAs), etc. Unless described otherwise, the construction and operation of the various blocks shown in FIG. 2 are of conventional design. As a result, such blocks need not be described in further detail herein, as they will be understood by those skilled in the relevant art.

The system bus 210 can employ any known bus structures or architectures, including a memory bus with memory controller, a peripheral bus, and a local bus. The system memory 208 includes read-only memory ("ROM") 212 and random access memory ("RAM") 214. A basic input/output system ("BIOS") 216, which can form part of the ROM 212, contains basic routines that help transfer information between elements within processor-based device 204, such as during start-up. Some embodiments may employ separate buses for data, instructions and power.

The processor-based device 204 may also include one or more solid state memories, for instance Flash memory or solid state drive (SSD) 218, which provides nonvolatile storage of computer-readable instructions, data structures, program modules and other data for the processor-based device 204. Although not depicted, the processor-based device 204 can employ other nontransitory computer- or processor-readable media, for example a hard disk drive, an optical disk drive, or memory card media drive.

Program modules can be stored in the system memory 208, such as an operating system 230, one or more application programs 232, other programs or modules 234, drivers 236 and program data 238.

The application programs 232 may, for example, include panning/scrolling 232a. Such panning/scrolling logic may include, but is not limited to logic that determines when and/or where a pointer (e.g., finger, stylus, cursor) enters a user interface element that includes a region having a central portion and at least one margin. Such panning/scrolling logic may include, but is not limited to logic that determines a direction and a rate at which at least one element of the user interface element should appear to move, and causes updating of a display to cause the at least one element to appear to move in the determined direction at the determined rate. The panning/scrolling logic 232a may, for example, be stored as one or more executable instructions. The panning/scrolling logic 232a may include processor and/or machine executable logic or instructions to generate user interface objects using data that characterizes movement of a pointer, for example data from a touch-sensitive display or from a computer mouse or trackball, or other user interface device.

The system memory 208 may also include communications programs 240, for example a server and/or a Web client or browser for permitting the processor-based device 204 to access and exchange data with other systems such as user computing systems, Web sites on the Internet, corporate intranets, or other networks as described below. The communications program 240 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 2 as being stored in the system memory 208, the operating system 230, application programs 232, other programs/modules 234, drivers 236, program data 238 and server and/or browser 240 can be stored on any other of a large variety of nontransitory processor-readable media (e.g., hard disk drive, optical disk drive, SSD and/or flash memory).

A user can enter commands and information via a pointer, for example through input devices such as a touch screen 248 via a finger 244a, stylus 244b, or via a computer mouse or trackball 244c which controls a cursor. Other input devices can include a microphone, joystick, game pad, tablet, scanner, biometric scanning device, etc. These and other input devices (i.e., "I/O devices") are connected to the processor(s) 206 through an interface 246 such as a touch-screen controller and/or a universal serial bus ("USB") interface that couples user input to the system bus 210, although other interfaces such as a parallel port, a game port or a wireless interface or a serial port may be used. The touch screen 248 can be coupled to the system bus 210 via a video interface 250, such as a video adapter to receive image data or image information for display via the touch screen 248. Although not shown, the processor-based device 204 can include other output devices, such as speakers, vibrator, haptic actuator or haptic engine, etc.

The processor-based device 204 operates in a networked environment using one or more of the logical connections to communicate with one or more remote computers, servers and/or devices via one or more communications channels, for example, one or more networks 214a, 214b. These logical connections may facilitate any known method of permitting computers to communicate, such as through one or more LANs and/or WANs, such as the Internet, and/or cellular communications networks. Such networking environments are well known in wired and wireless enterprise-wide computer networks, intranets, extranets, the Internet, and other types of communication networks including telecommunications networks, cellular networks, paging networks, and other mobile networks.

When used in a networking environment, the processor-based device 204 may include one or more network, wired or wireless communications interfaces 252a, 256 (e.g., network interface controllers, cellular radios, WI-FI radios, Bluetooth radios) for establishing communications over the network, for instance the Internet 214a or cellular network.

In a networked environment, program modules, application programs, or data, or portions thereof, can be stored in a server computing system (not shown). Those skilled in the relevant art will recognize that the network connections shown in FIG. 2 are only some examples of ways of establishing communications between computers, and other connections may be used, including wirelessly.

For convenience, the processor(s) 206, system memory 208, and network and communications interfaces 252a, 256 are illustrated as communicably coupled to each other via the system bus 210, thereby providing connectivity between the above-described components. In alternative embodiments of the processor-based device 204, the above-described components may be communicably coupled in a different manner than illustrated in FIG. 2. For example, one or more of the above-described components may be directly coupled to other components, or may be coupled to each other, via intermediary components (not shown). In some embodiments, system bus 210 is omitted and the components are coupled directly to each other using suitable connections.

Figure 3:
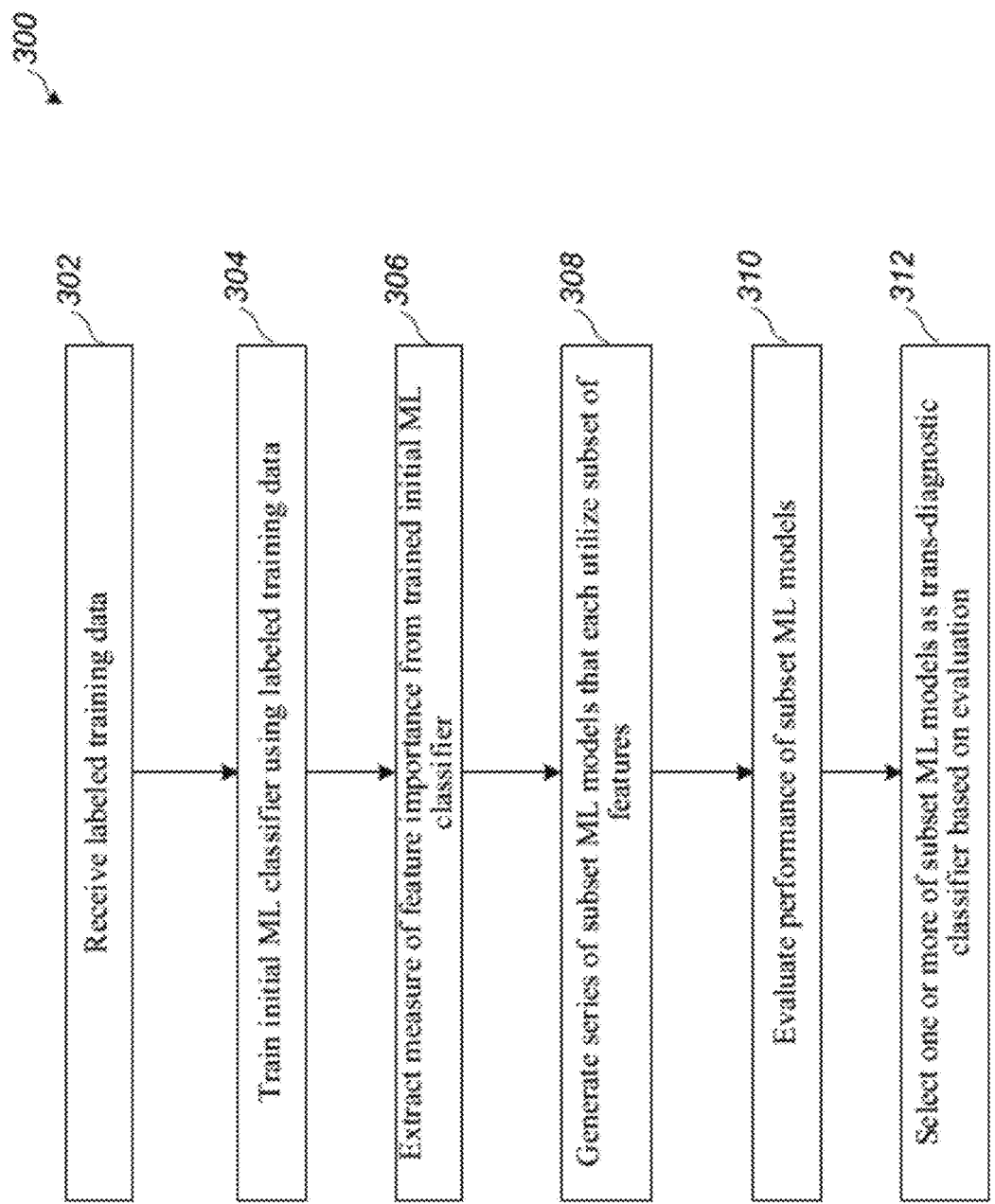
FIG. 3 is a flow diagram for a method of operating a trans-diagnostic classifier system according to one illustrated implementation of the present disclosure.

FIG. 3 is a high level flow diagram of a method 300 of operating a TDC system in accordance with the techniques of the present disclosure. The method 300 may, for example, be performed by TDC system 100 of FIG. 1.

The method 300 begins at 302, wherein at least one processor of the TDC system receives labeled training data. As discussed above, the labeled training data may include data for a plurality of individuals that indicates whether each of the individuals has one or more of a plurality of mental health disorders, such as, but not limited to, schizophrenia, bipolar disorder, or attention deficit and hyperactivity disorder (ADHD). For each of the individuals, the labeled training data also includes item-level responses to multiple self-administered mental health questionnaires (e.g., five questionnaires, 10 questionnaires, 20 questionnaires). In some examples, the training data includes video data and audio data recorded while each of the plurality of individuals read text from a digital display. In some examples, the video data is processed to identify portions of the video data comprising the face of the individual, and the audio data is processed to identify sounds representing the voice of the individual In at least some implementations, the labeled training data comprises a dataset that is publicly-available from the UCLA Consortium for Neuropsychiatric Phenomics, which focused on the understanding of the dimensional structure of memory and cognitive control functions in both healthy individuals (130 subjects) and individuals diagnosed as having neuropsychiatric disorders including schizophrenia (50 subjects), bipolar disorder (49 subjects), and ADHD (43 subjects) after administration of the Structured Clinical Interview for DSM Disorders by mental health professionals.

All participants provided item-level responses to multiple self-administered mental health questionnaires. In the example embodiment discussed herein, individuals' responses to a total of 578 individual questions were used. The questions were obtained from the following scales/questionnaires: Hopkins Symptom Checklist (HSCL); Adult Self-Report Scale v1.1 Screener (ASRS); Barratt Impulsiveness Scale (BIS-11); Dickman Functional and Dysfunctional Impulsivity Scale; Multidimensional Personality Questionnaire (MPQ)—Control subscale; Impulsiveness, Venturesomeness and Empathy Scale (IVE); Scale for Traits that Increase Risk for Bipolar II Disorder; Golden & Meehl's Seven MMPI Items Selected by Taxonomic Method; Hypomanic Personality Scale (HPS); Chapman Scales (Perceptual Aberrations, Social Anhedonia, Physical Anhedonia); and Temperament and Character Inventory (TCI). It should be appreciated that in other implementations, one or more different scales/questionnaires may be used, or various combinations of one or more scales/questionnaires.

Figure 4:
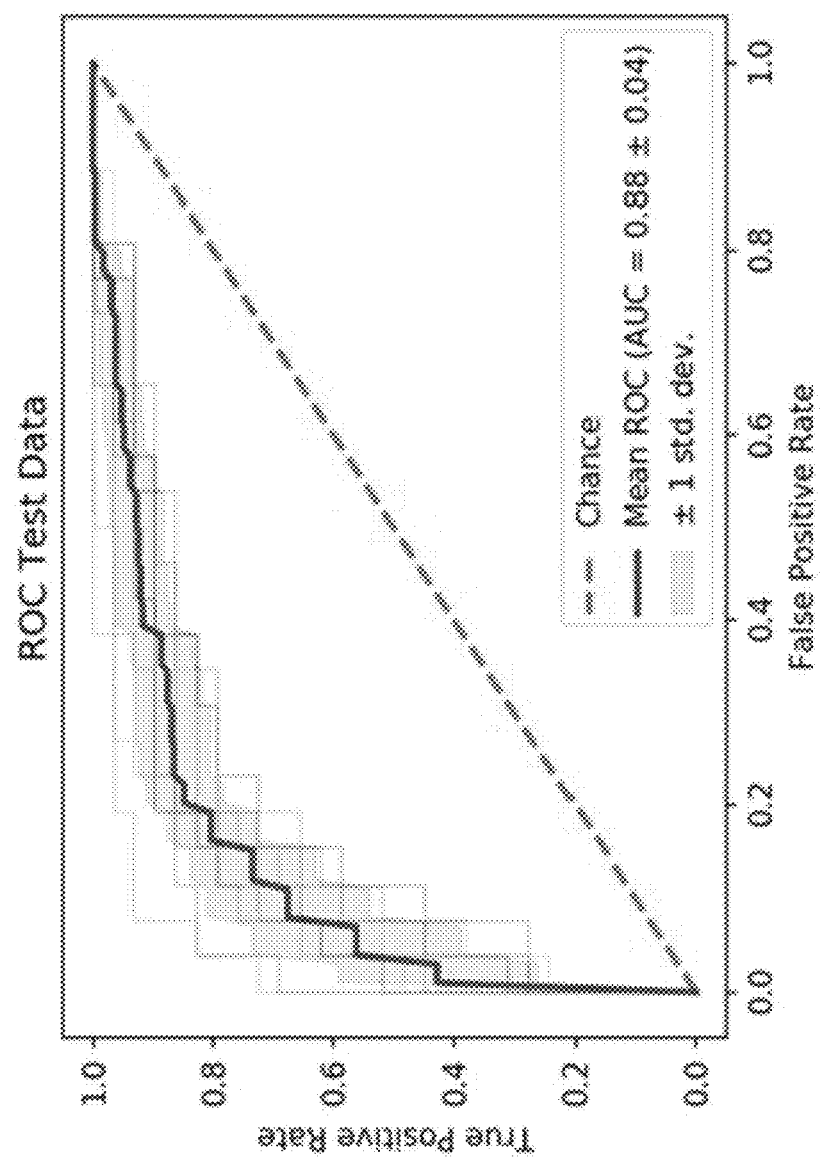
FIG. 4 is a graph that shows the receiver operating characteristics (ROC) curve for an initial machine learning classifier, according to one non-limiting illustrated implementation of the present disclosure.

At 304, at least one processor of the TDC system trains an initial machine learning classifier or model using the labeled training data. For example, in at least some implementations, k-fold cross-validation (e.g., 10-fold cross-validation) with logistic regression is used to classify healthy control (HC) individuals from patients diagnosed with one or more mental health disorders base on the scores of the 578 individual questions. Using all of the individual questions, the system was operative to classify subjects as either "HC" or "Patient" with a mean accuracy of 79%. FIG. 4 is a graph 400 that shows the receiver operating characteristics (ROC) curve, another evaluation metric, which had a mean area under the curve (AUC) of 0.88 (max 1).

At 306, the at least one processor of the TDC system extracts or obtains a measure of feature importance for the 578 questions or features from the regression coefficients.

At 308, in order to examine if shortening the list of questions could provide comparable classification ability, the TDC system generates a series of models, also referred to herein as subset ML models, sequentially adding in features in order of importance, starting with the most important feature. For example, a first subset ML model may include only the most important feature, a second subset ML model may include the two most important features, a third subset ML model may include the top three most important features, etc.

Figure 5:
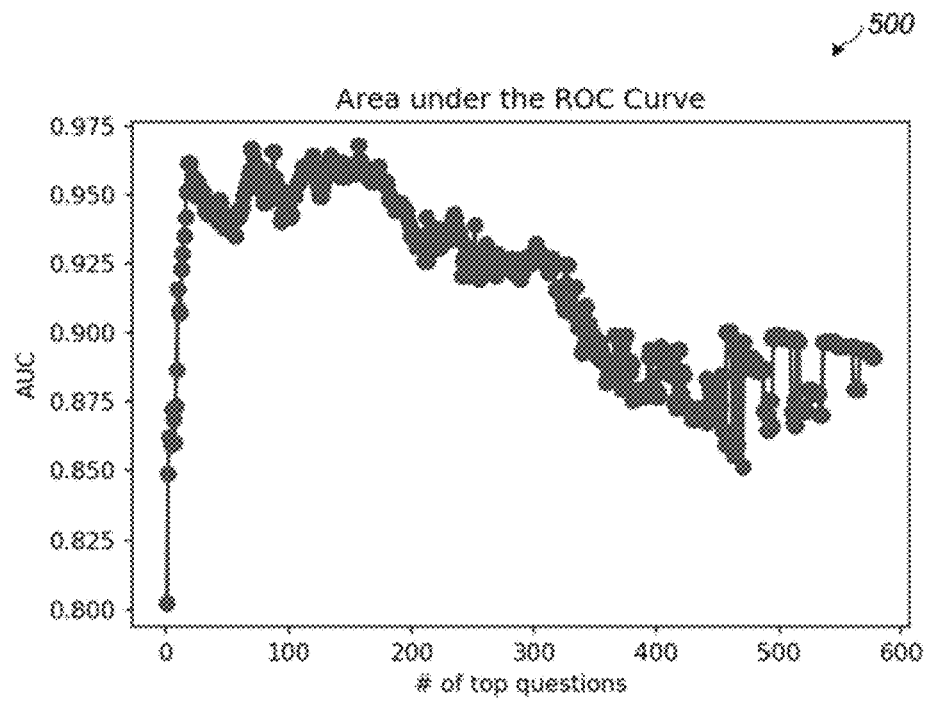
FIG. 5 is a graph that shows the area under the ROC curve for a plurality of subset machine learning models that include from one feature up to 578 features, according to one non-limiting illustrated implementation of the present disclosure.
Figure 6:
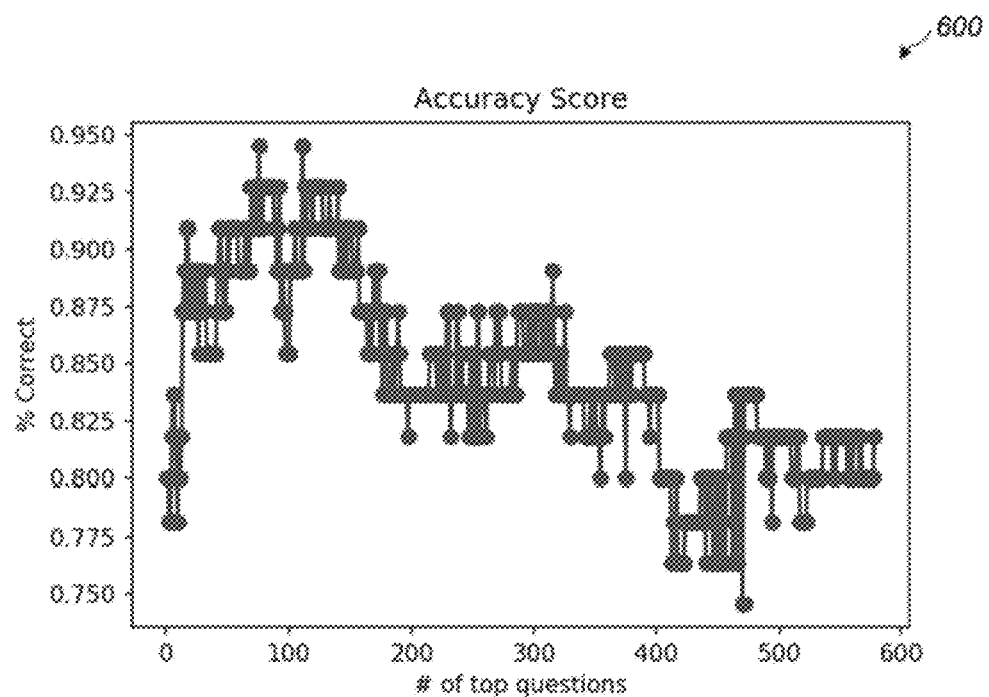
FIG. 6 is a graph that shows an accuracy score for the plurality of subset machine learning models, according to one non-limiting illustrated implementation of the present disclosure.

At 310, at least one processor of the TDC system may evaluate the performance of at least some of the generated subset ML models. FIG. 5 is a graph 500 that shows the area under the ROC curve for the subset ML models that include from one feature (i.e., the most important feature) up to the all of the features. FIG. 6 is a graph 600 that shows an accuracy score for each of the subset ML models.

It was found that classifier performance across different subsets of questions (i.e., questions 1 through 578) varied on AUC from 0.8 to 0.97. Further, it was found that only 17 features are needed for an accuracy of 91% and 0.95 AUC. This indicates that more features are not necessarily better in a classifier-based screen. Notably, the top 17 features included a disproportionate number of questions regarding personality and temperament with additional questions on impulsivity, mood, and mania. In an example embodiment, the 17 top features or questions include the following questions, in order starting with the most important feature:

(1) "I like to please other people as much as I can" (tci28t);
(2) "There are often times when I am so restless that it is impossible for me to sit still" (chaphypo8);
(3) "My mood often changes, from happiness to sadness, without my knowing why" (bipolarii1);
(4) "Although there are things that I enjoy doing by myself, I usually seem to have more fun when I do things with other people" (chapsoc8);
(5) "I am more sentimental than most people" (tci55t);
(6) "I love to excel at everything I do" (tci72p);
(7) "People consider me a rather freewheeling and spontaneous person" (mpq243);
(8) "I feel that I never really get all that I need from people" (bipolarii26);
(9) "In unfamiliar surroundings, I am often so assertive and sociable that I surprise myself" (chaphypo7);
(10) "I like to think about things for a long time before I make a decision" (tci61t);
(11) "Sometimes ideas and insights come to me so fast that I cannot express them all" (chaphypo5);
(12) "I have many hobbies" (dicks);
(13) "I like to keep my problems to myself" (tci68t);
(14) "It is difficult for me to keep the same interests for a long time because my attention often shifts to something else" (tci35t);
(15) "How often do you have trouble wrapping up the final details of a project, once the challenging parts have been done" (finaldetail);
(16) "I like to go slow in starting work, even if it is easy to do" (tci189p); and
(17) "Usually I am more worried than most people that something might go wrong in the future" (tci81t).

As would be readily understood by one skilled in the art, variations of these questions can be used in the disclosed systems and methods as well. In various examples of the present disclosure, some additional questions can be used, replacement/alternate questions can be used, or some of the questions can be omitted.

At 312, at least one processor of the TDC system selects one or more of the subset ML models as a trans-diagnostic classifier based on the performance evaluation. For example, at least one processor of the TDC system may select the subset ML model that includes the above-listed top 17 features as a trans-diagnostic classifier. The selected trans-diagnostic classifier may then be used to screen subjects across multiple mental health disorders without physician involvement, optionally remotely and repeatedly, in a short period of time (e.g., less than 5 minutes).

In at least some implementations, the above described techniques may additionally or alternatively be used to generate a specific screen for individual diagnoses, for example, a screen that classifies Healthy vs. Schizophrenic, or a screen that classifies Healthy vs. Bipolar, etc. Similar to the trans-diagnostic screen discussed above, each of these screens may include an associated shortlist of questions determined using the techniques used herein that allow for quick-screening relative to existing screening methods.

Exemplary Screening System

Figure 7A:
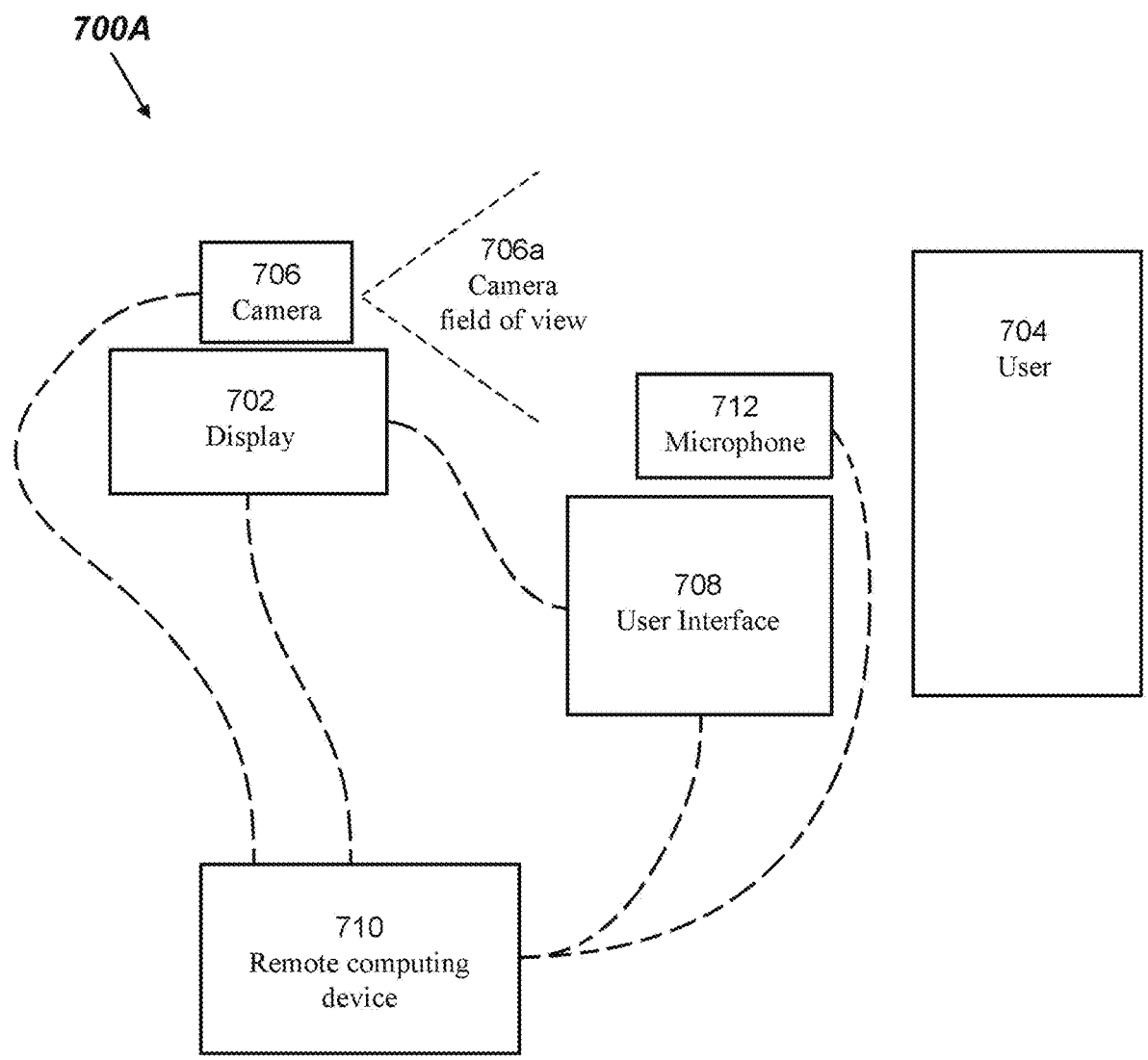
FIG. 7A provides an exemplary system, according to an embodiment of the present disclosure.

The present disclosure contemplates that a variety of systems can be used to perform various embodiments of the present disclosure. FIG. 7A presents an exemplary system 700A, which can be configured to perform various methods of the present disclosure, including methods 720, 730, 740, 800, and 900 of FIGS. 7B, 7C, 7D, 8, and 9, respectively. In particular, system 700A includes a display 702; a user 704; a camera 706; a camera field of view 706*a*; a user interface 708; a remote computing device 710; and a microphone 712.

The camera 706 captures visual data of an area in front of the camera (area 706*a*) and transmits the visual data to the display 702 and the remote computing device 710. As shown in FIG. 7A, a user 704 sits in the view of the camera 706. In such an example, the camera 706 captures footage of the face of the user 704. In some examples, the camera 706 can be configured to take live video footage, photographs, or images/videos in non-visual wavelengths. In some examples, the camera 706 is configured to start or stop recording based on instructions from the remote computing device 710 or a local processor or computing device. For instance, the application or program running the process may be performed by a remote server, computing device, or a local processor. The camera 706 is communicatively coupled to the display 702 and the remote computing device 710 or a local computing device. In some examples, a smartphone will perform each of these functions.

The user interface 708 is configured to receive input from a user 704. For example, the user interface 708 can be a keyboard, a touchscreen, a mobile device, or any other device for receiving input, as known in the art. The user 704 enters data on the user interface 708 in response to prompts on the display 702. For example, the display 702 outputs a series of mental health questions, and the user 704 inputs an answer to each question on the user interface 708. The user interface 708 is configured to directly display the input on display 702 and is configured to relay the data to the remote computing device 710.

The microphone 712 is configured to receive auditory input, for example, from the user 704. The microphone is configured to start or stop recording based on instructions from the remote computing device 710. The microphone is configured to transmit audio data to the remote computing device 710. In some examples, the microphone can be on a user's smart phone.

The display 702 is configured to receive data from the camera 706, the remote computing device 710, and the user interface 708. For example, the display 702 displays the visual data captured by the camera 706. In another example, the display 702 displays input received from the user interface. The display 702 is directly coupled to the camera 706 and the microphone 712 in some examples; in other examples, the camera 706 and the microphone 712 send their data to the remote computing device 710, which then processes the data and instructs the display 702 according to the processed data. In other examples, the display 702 displays data received from the remote computing device 710. Exemplary data from the remote computing device 710 includes questions from a mental health questionnaire, answer boxes, answer options, answer data, a mental health indicator, or any other information. In some examples, the display 702 is on a smart phone.

The present disclosure also contemplates that more than one display 702 can be used in system 702, as would be readily contemplated by a person skilled in the art. For example, one display can be viewable by the user 704, while additional displays are visible to researchers and not to the user 704. The multiple displays can output identical or different information, according to instructions by the remote computing device 710.

A remote computing device 710 can be communicatively coupled to a display 702, a camera 706, a user interface 708, and a microphone 712. For example, the communication can be wired or wireless. The remote computing device 710 is configured to perform any methods as contemplated according to FIGS. 7B-9 (discussed further below). The remote computing device 710 can process and/or store input from the display 702, the camera 706, the user interface 708, and the microphone 712.

Figures 10A, 10B:
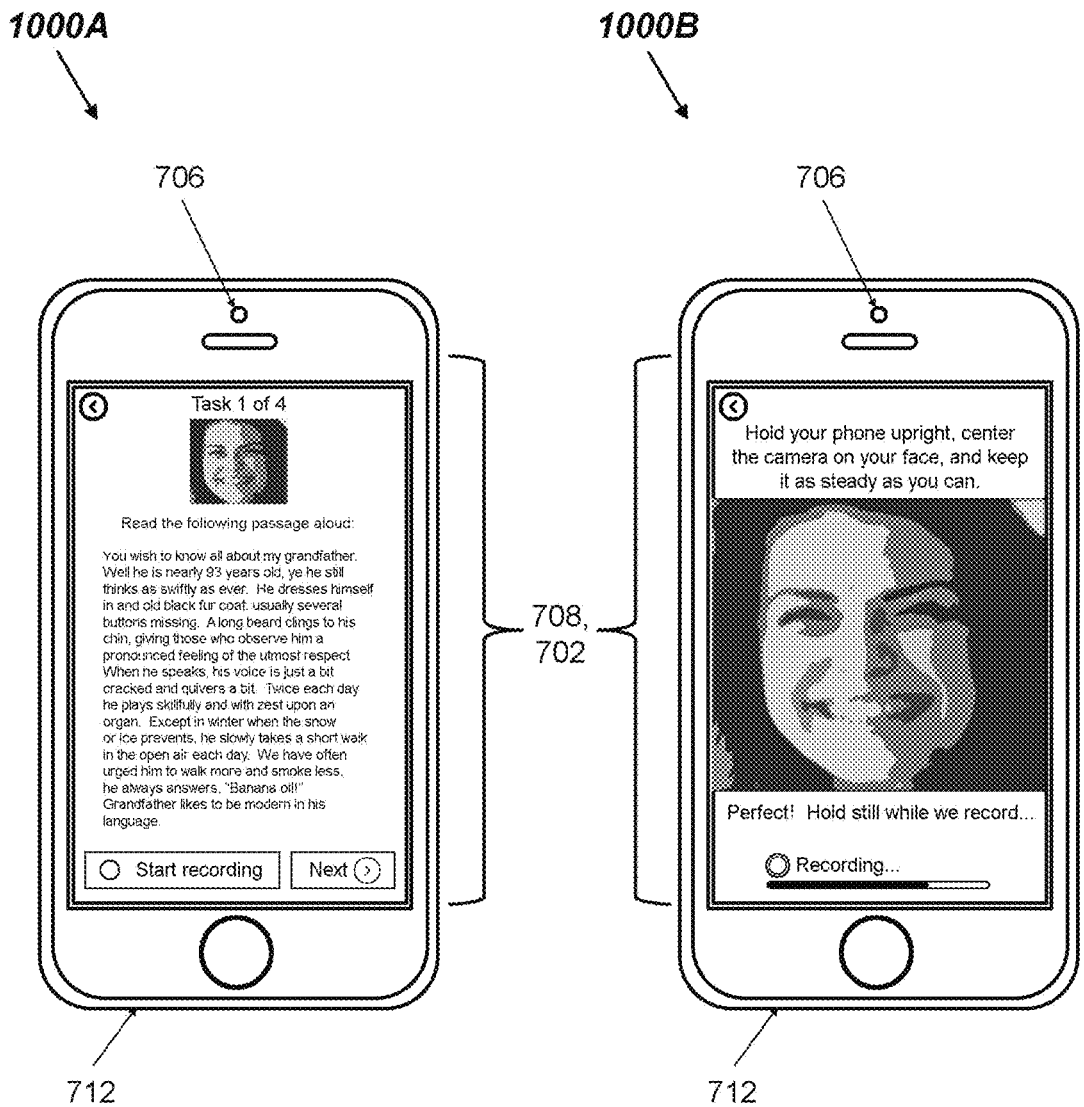
FIGS. 10A-10B show exemplary user interfaces on a smart phone, according to an embodiment of the present disclosure.

In some examples, system 700 can be a user 704 with a unitary device, for example, a smart phone. The smart phone can have a display 702, a camera 706, a user interface 708, a computing device 710, and a microphone 710. For example, the user 704 can hold the smart phone in front of his or her face while reading text on the display 702 and responding to the mental health questionnaires. Referring briefly to FIGS. 10A-10B, an exemplary interface design is shown. Similar labels are used for corresponding elements to FIG. 7A. FIG. 10A shows a screen 1000A displaying text for a user to read, and FIG. 10B shows a screen 1000B displaying a user's face as video data is being recorded. FIGS. 10A-10B demonstrate how the disclosed system and methods can be performed on a local device, with ease of access for the user.

Test Application for Voice/Facial Recognition during Screening

Figure 7B:
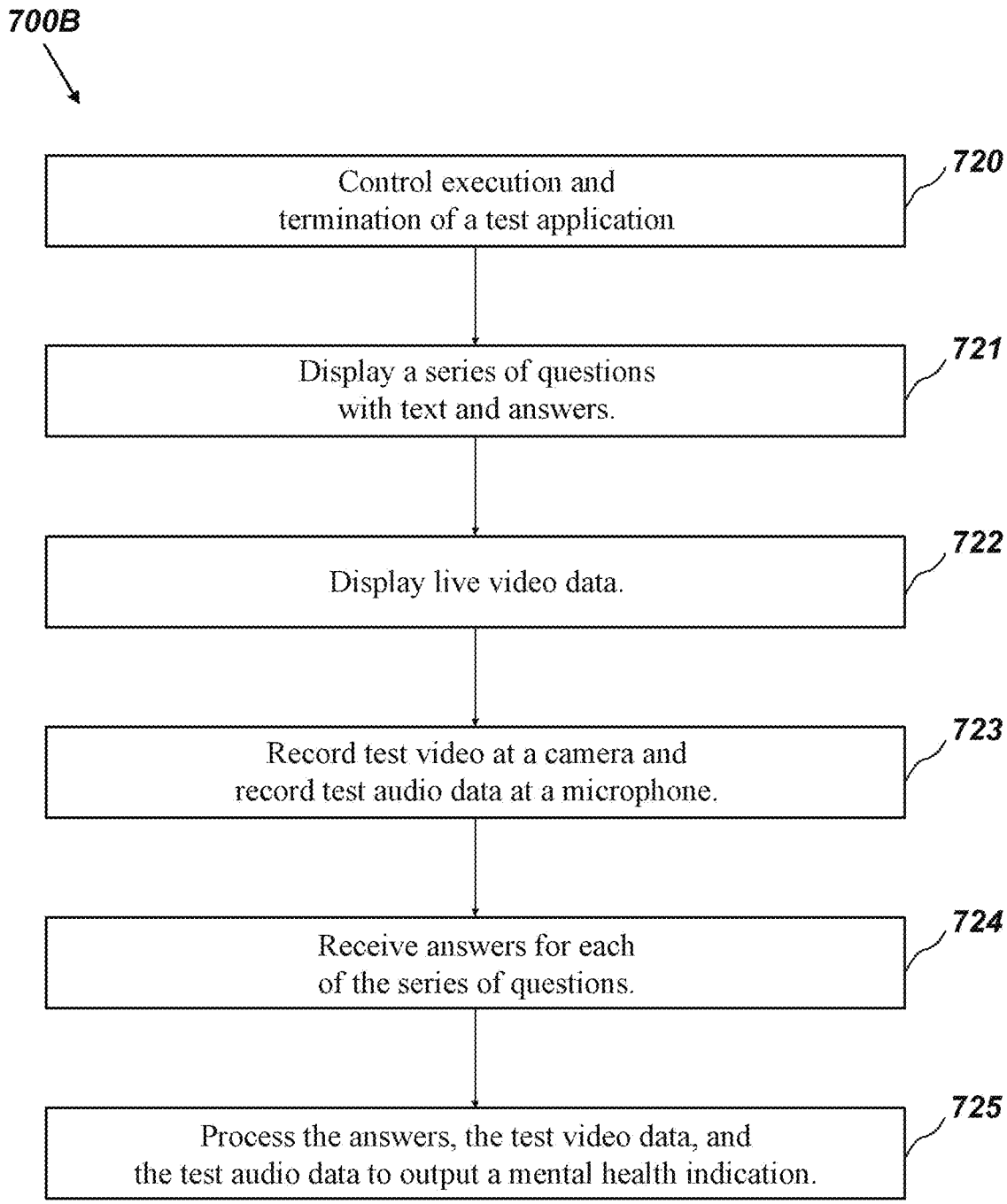
FIGS. 7B-7D show exemplary methodologies for receiving and analyzing data, according to an embodiment of the present disclosure.

FIG. 7B shows an exemplary methodology 700B, according to an exemplary implementation of the present disclosure. Methodology 700B provides a test for a user and can be provided for by the system 700A, as discussed above with respect to FIG. 7A.

Methodology 700B provides for, at step 720, controlling execution and termination of a test application. The test application can be a software application stored on a computing device (e.g., the remote computing device 710 of FIG. 7A). Step 720 provides for executing the test application upon receiving and indication to initiate a test. In some examples, the indication comes from a user interface (e.g., the user interface 708 of FIG. 7*a*) communicatively coupled to the computing device.

Step 720 provides for executing the test application until the computing device receives an indication to stop the test. In some examples, this indication comes from the user interface. In some examples, the indication to stop the test includes determining, by the computing device, that the user's face is not within an image captured by a camera.

While the test is being executed according to step 720, methodology 700B proceeds to step 721. Step 721 provides for displaying a series of questions. An exemplary series of questions includes questions from mental health questionnaires, and includes both text and answers for each question.

While the test is being executed according to step 720, methodology 700B can provide for step 722. Step 722 provides for displaying live video data. In some examples, live video data is collected from a camera positioned to capture an image in front of a display (e.g., camera 706 capturing visual data of user 704 positioned in front of the display 702, as shown in FIG. 7A). In some examples, live video data is recorded and then displayed at a display; in other examples, live video data is simultaneously recorded and displayed. The display can be facing the user.

While the test is being executed according to step 720, methodology 700B can provide for step 723. Step 723 provides for recording test video data and test audio data (e.g., from camera 706 and microphone 712 of FIG. 7A). In some examples, the audio data and the video data are recorded in segments corresponding to the display of questions at step 722; in others examples, the data is collected in an un-interrupted stream while the questions are presented at step 722. In some examples of step 723, the video and audio data is pre-processed according to methodology 730 of FIG. 7C.

In some examples, a microphone (e.g., microphone 712 of FIG. 7A) records audio data upon determining, by the computing device, that the user is speaking. In some examples, the microphone stops recording audio data when the computing device determines that the user is not speaking.

While the test is being executed according to step 720, methodology 700B can provide for step 724. Step 724 provides for receiving answers for each of the series of questions (the questions provided for in step 721). The answers are received at a user interface. In some examples, the answers include selection of a multiple choice question, a textual response, or any other user input as contemplated by one skilled in the art.

While the test is being executed according to step 720, methodology 700B can provide for step 725. Step 725 provides for processing the answers received at step 724 and the test video data and the test audio data recorded at step 723. In some examples, the processing is performed at a computing device using a machine learning model and outputs a mental health indication of the user. In some examples of the present disclosure, step 725 performs processing of the answers, the test video data, and the test audio data as discussed further below with respect to method 740 of FIG. 7D.

In some examples, the output mental health indication identifies a likelihood of the user having any one of several mental health disorders. The mental health disorders include a neuropsychiatric disorder, schizophrenia, and a bipolar disorder. In some examples, the mental health indication identifies whether the user is a patient or a healthy control.

Steps 721, 722, 723, 724, and 725 of FIG. 7B can occur sequentially after the test application is initiated in step 720. In some examples of methodology 700B, steps 721, 722, 723, 724, and 725 occur simultaneously and/or in any combination. In some examples of methodology 700B, portions of steps 721, 722, 723, 724, and 725 or any subsets of steps 721, 722, 723, 724, and 725 are repeated or omitted according to instructions from a remote computing device. Therefore, the present disclosure contemplates that any combination of the above description of steps 720, 721, 722, 723, 724, and 725 can be used in an embodiment of the present disclosure, as readily contemplated by one skilled in the art.

Figure 7C:
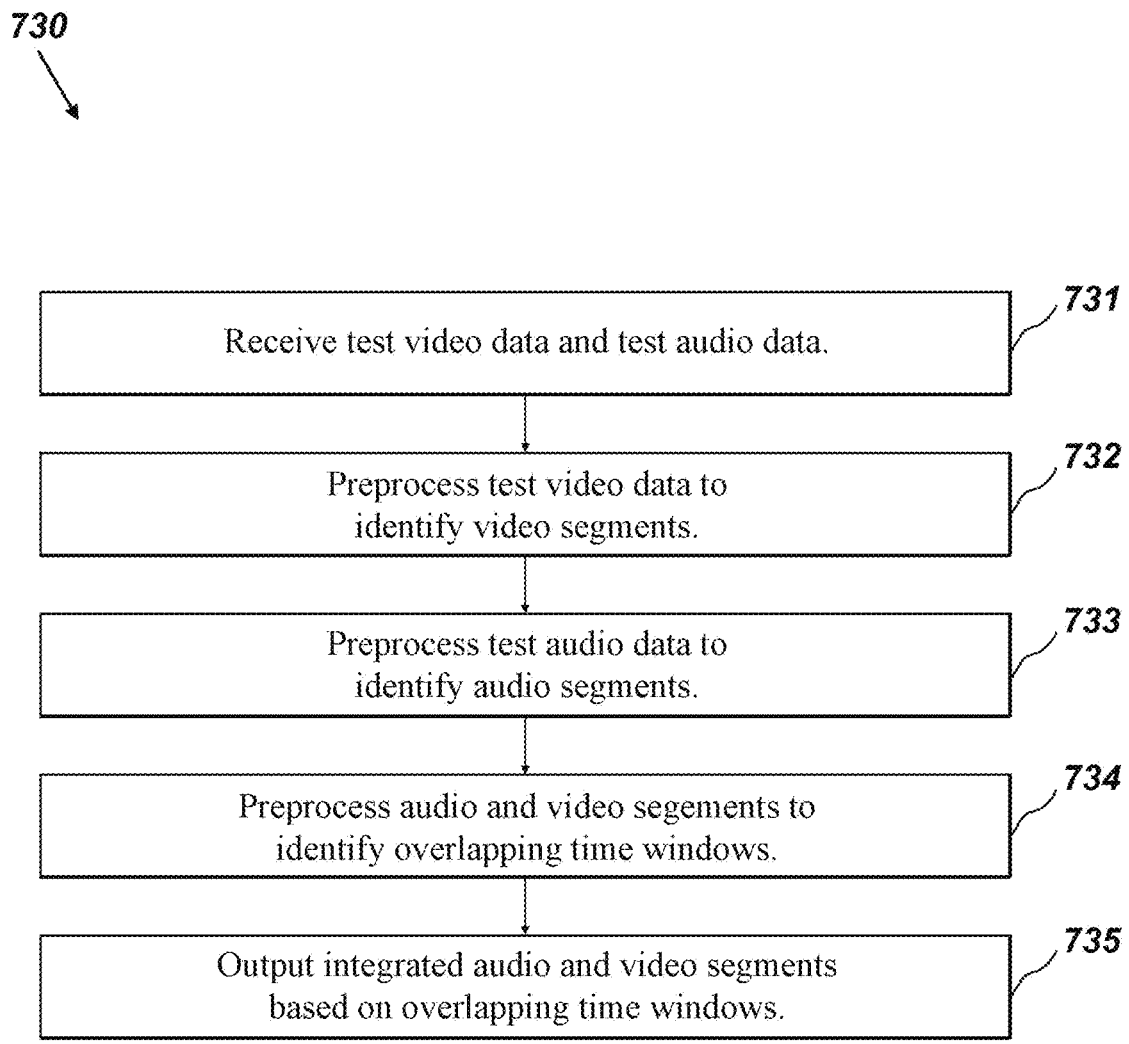

Referring now to methodology 730 of FIG. 7C, an exemplary methodology is shown for preprocessing audio and visual data, according to various embodiments of the present disclosure. In step 731, methodology 730 provides for receiving test video data and test audio data. In some examples, the test video data and test audio data are recorded according to methodology 700B of FIG. 7B, or another embodiment of the present disclosure.

Step 732 provides for preprocessing the test video data to identify video segments. Each video segment corresponds to one question in a series of questions (e.g., questions from a test, as discussed with respect to methodology 700B of FIG. 7B) and includes a time window; the time window provides a duration of the video segment and a period of time in the recorded data during which the video segment occurs. In some examples, the time window includes any of: a start time, a stop time, and a duration length. In some examples, video segments are identified based on instructions from a computing device according to when questions were displayed at a display.

Step 733 provides for preprocessing the test audio data to identify audio segments. Each audio segment corresponds to one question in the series of questions and includes a time window; the time window is as provided with respect to the time windows of step 732. In some examples, audio segments are identified based on instructions from a computing device according to when questions were displayed at a display. In some examples, audio segments are identified based on a computing device determining whether a user is speaking.

Step 734 provides for preprocessing the video segments of step 732 and the audio segments of step 733 to identify overlapping time windows. Step 735 provides for outputting integrated audio and video segments based on overlapping time windows. In some examples, the integrated audio and video segments are stored on a remote computing device.

Figure 7D:
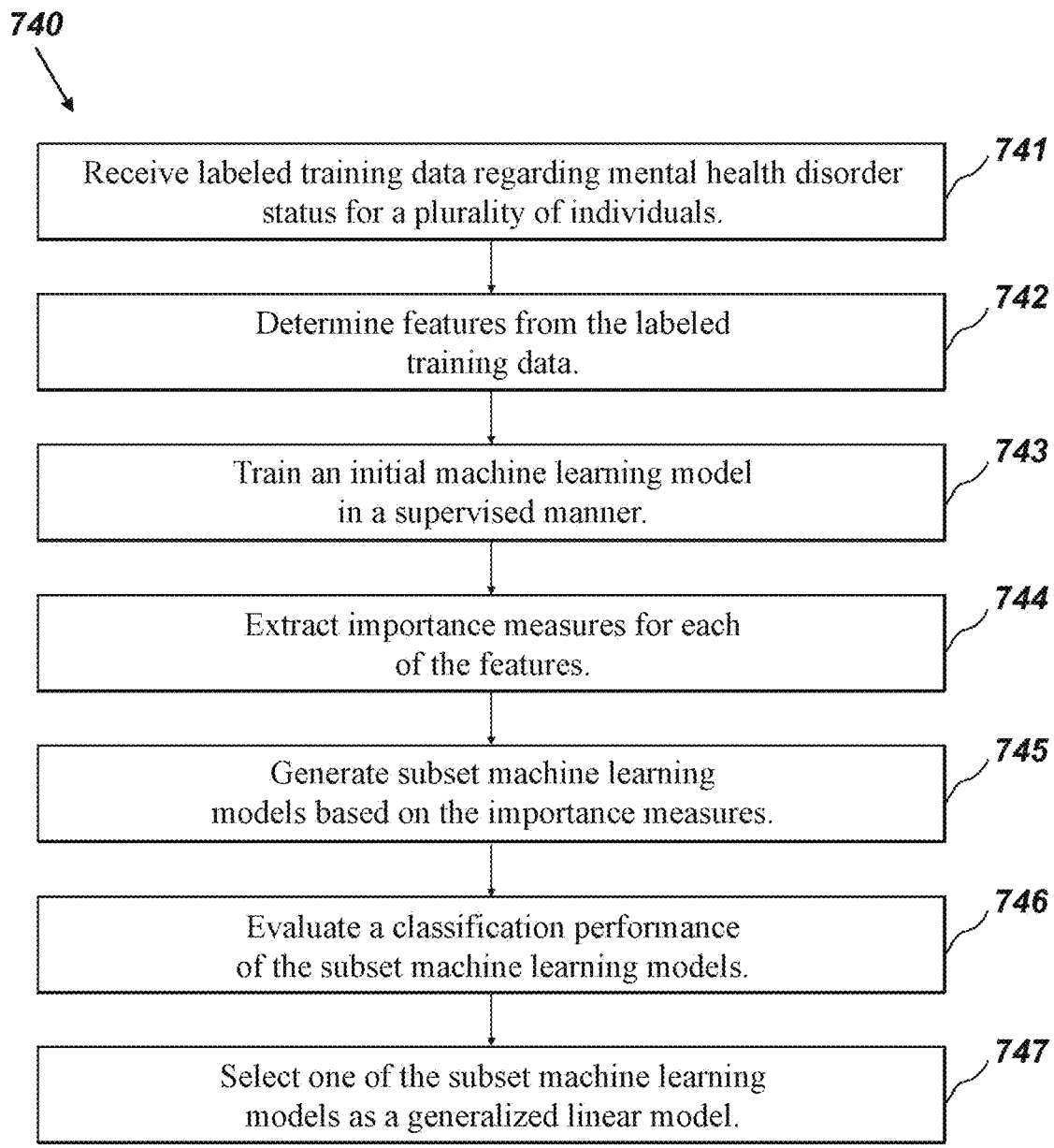

Referring now to methodology 740 of FIG. 7D, an exemplary methodology is shown for using a machine learning model to analyze input and output a mental health indication, according to various embodiments of the present disclosure. In some examples, the machine learning model is any of: a generalized linear model, a regression model, a logistical regression model, and a supervised machine learning classification model. In some examples, the machine learning model is any of the models and algorithms discussed further below.

In step 741, methodology 740 provides for receiving labeled training data regarding mental health disorder status for a plurality of individuals. In some examples, the labeled training data identifies whether each of the individuals has one or more mental health disorders. In some examples, the labeled training data includes audio and video data recorded for each of the individuals (e.g., audio and video data recording according to methodology 700B of FIG. 7B, or any other embodiment of the present disclosure). The labeled training data can also a selection of answers to mental health questionnaires. In some examples, the labeled training data includes, for each individual, an indication of any of: whether the individual is healthy, whether the individual has a general mental health issue, whether the individual has one or more specific mental health disorders, whether the individual is at risk of developing a general mental health issue, or whether the individual is at risk of developing one or more specific mental health disorders. In some examples, the labeled training data includes functional and/or physiological measurement data.

In step 742, methodology 740 provides for determining features from the labeled training data of step 714. The features are determined according to any methods, as known in the art.

In step 743, methodology 740 provides for training an initial machine learning model in a supervised manner, based on the features determined in step 742. In some examples, training this initial machine learning model includes using k-fold cross-validation with logistic regression.

In step 744, methodology 740 provides for extracting importance measures for each of the features. These importance measures are selected based on the trained initial machine learning model.

In step 745, methodology 740 provides for generating a plurality of subset machine learning models, based on the extracted importance measures of step 744. In step 746, methodology 740 provides for evaluating a classification performance of the generated subset machine learning models from step 745. In some examples, each of the subset machine learning models includes a different selection of features. In some examples, the subset machine learning models include only features with an importance measure above a threshold value.

In step 747, methodology 740 provides for selecting one of the subset machine learning models as a generalized linear learning model. The selection is based on the classification performances as evaluated in step 746. The selected subset machine learning model includes a portion of the plurality of features determined from step 742. The portion of features is selected from features with an importance measure (as determined in step 744) above a threshold value. In some examples, more than one subset machine learning model is selected.

In some examples of step 747, the threshold value is set so that at least twenty features of the plurality of features determined in step 742 have an importance measure above the threshold value. In some examples, the threshold value is set to select a portion of between ten and twenty features.

In some examples of step 747, at least one of the subset machine learning models is selected as a diagnostic classifier. The features of the diagnostic classifier are stored in a remote computing device for subsequent use as a screening tool. In some examples, the diagnostic classifier outputs a mental health indication. The mental health indication can be any of: (1) identifying a user as healthy or as having a general mental health issue, (2) identifying the user as healthy or as having a specific mental health issue, (3) identifying the user as having either a first specific mental health disorder or a second specific mental health disorder, and (4) identifying a risk of developing a mental health disorder for an individual.

The selected machine learning model can then be used to process any of the input data as provided for in the present disclosure. In some examples, the features of the diagnostic classifier are used as a screening tool to assess intermediate and/or end-point outcomes in clinical trial testing for treatment responses.

Overall, methods 720 of FIG. 7B and 730 of FIG. 7C provide algorithms which receive input in different modalities. Methodology 740 provides processing of the input from methods 720 and 730 to output an algorithm based on features that have the highest predictive value (predictive value can be determined based on importance measures). For example, various embodiments of methods 720 and 730 receive mental health questionnaire data, voice data, and/or video data. Methodology 740 receives all the input, determines features based on the input, and determines which of those features have the highest predictive value. A machine learning model can be built which incorporates the features with the highest predictive value.

Accordingly, the model, methodology, and model builder are especially valuable and designed for efficiently combining features from multiple modalities including various different scales instruments, video data and audio data to build multi-modal models that can frequently be more accurate than single modality models. For instance, prior technology required a new model to be built and trained for each new combination of modalities, which made it completely impractical to combine modalities efficiently, especially without introducing too much noise in the outputs as prior technology cannot test features from various modalities to incorporate them into a single model. Particularly, in some examples, additional features may be less accurate, and therefore one key to combining modalities is to incorporate the right features from each modality. The disclosed technology provides processes and models that allow for their efficient testing and combination.

Furthermore, mental health screeners and models frequently benefit from examining more than one modality and may produce far superior accuracy in some examples. For instance, processing only answers from scales based questions may fail to capture the tone of voice and facial expressions made while reading a statement—and other things like the speed at which the statement is read. This features may be critically important to an assessment of the mental health of a patient, as for example, a statement may be read in various tones of voice, or spoken with the same tone of voice but with different facial expressions—all conveying different emotions and mental health status indicators.

This model can then be used as a diagnostic tool. For example, additional mental health questionnaire data, voice data, and/or video data can be input into the model to determine a mental health indication of a patient.

Therefore, the methods of the present disclosure provide machine learning algorithms which can determine the features that are predictive for various mental health disorders. For example, the machine learning model can determine a mental health indication related to a first particular mental health disorder relies on a first set of features; this first set of features can be from any input modality (e.g., a depression mental health indication can rely on tone of voice and facial expression). The machine learning model can further determine that a mental health indication related to a second particular mental health disorder relies on a second set of features; this second set of features can be from any input modality (e.g., an anxiety mental health indication can rely on stuttering audio data or frequent self-references of the speaker). Accordingly, different features can be deterministic for different mental health disorders; however, the same algorithm can be used for different mental health disorders and for different input data. In some examples, the disclosed algorithm automatically adjusts which mental health indications can be provided based on what input data is provided.

Application for Collecting Audio and Video Recording

Figure 8:
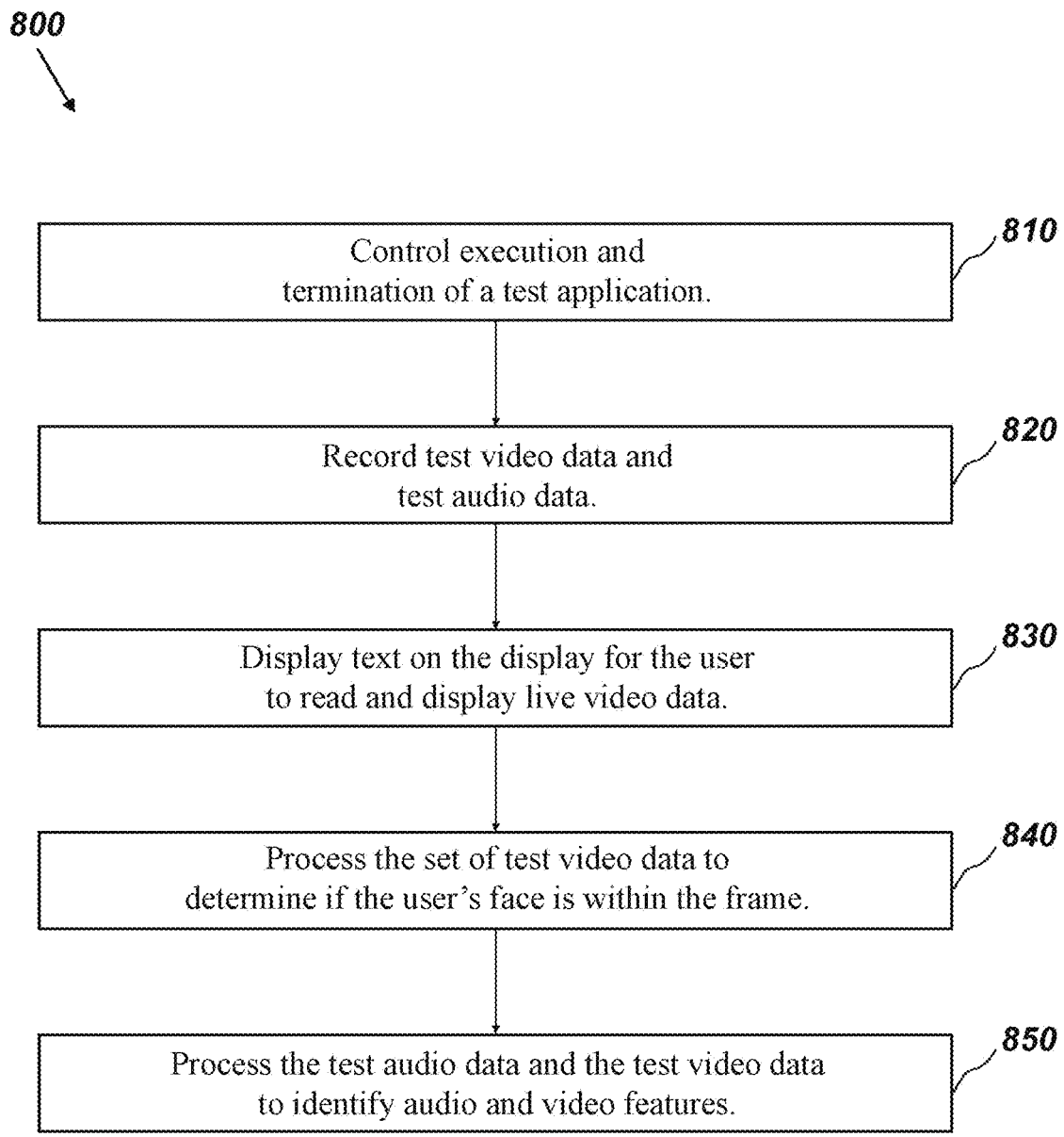
FIG. 8 shows an exemplary methodology of processing audio and video data, according to an embodiment of the present disclosure.

FIG. 8 shows an exemplary methodology 800, according to an exemplary implementation of the present disclosure. Methodology 800 provides a method of administering a test to a user and can be provided for by the system 700A, as discussed above with respect to FIG. 7A.

Methodology 800 provides for, at step 810, controlling execution and termination of a test application. The test application can be a software application stored on a computing device (e.g., the remote computing device 710 of FIG. 7A). Step 810 provides for executing the test application upon receiving and indication to initiate a test While the test is being executed according to step 810, methodology 800 can provide for step 820. Step 820 provides for recording test video data and test audio data. The test video data can be captured by a camera (e.g., camera 706 of FIG. 7A) and the test audio data can be captured by a microphone (e.g., microphone 712 of FIG. 7A).

While the test is being executed according to step 810, methodology 800 can provide for step 830. Step 830 provides for displaying live video data recorded by a camera and displaying text on the display for the user to read. In some examples, the text includes a series of questions or statements related to the user's mental health. The microphone captures audio data when the user reads the text aloud. In some examples, the displayed text includes a series of questions from mental health questionnaires, including question text and answer selections for each question.

While the test is being executed according to step 810, methodology 800 can provide for step 840. Step 840 provides for processing the set of test video data recorded at step 820 to identify a face of the user and determine when the user's face is within the camera field of view. In some examples, step 840 further comprises assigning a plurality of pixels to the user's face and determining whether all of the plurality of pixels of the user's face are within a frame captured by the camera. If the face is determined to be outside the frame captured by the camera, step 840 provides for stopping the test. In other examples of step 840, a plurality of pixels are assigned to a boundary of the user's faced, and the step further provides for determining whether the boundary of the user's face is within a frame captured by the camera. The present disclosure further contemplates that any method can be used to ensure that a user's face is within the camera's view, as known in the art.

While the test is being executed according to step 810, methodology 800 can provide for step 850. Step 850 provides for processing the test audio data and the test video data to identify audio and video features. The audio and video features are stored in a memory of a computing device. In some examples of step 850, processing the test audio data and the test video data is as provided for with respect to method 740 of FIG. 7D above. In some examples, the audio and video features correspond to particular questions in the series of questions.

In some examples, before, during, or after step 850, methods 730 and 740 of FIGS. 7C and 7D are applied to the test audio data and test video data, as would be readily contemplated by one skilled in the art.

In some examples of methodology 800, steps 820, 830, 840, and 850 occur sequentially after the test application is initiated in step 810. In some examples, steps 820, 830, 840, and 850 occur simultaneously and/or in any combination. In some examples, portions of steps 820, 830, 840, and 850 or any subsets of steps 820, 830, 840, and 850 are repeated or omitted according to instructions from a remote computing device. Therefore, the present disclosure contemplates that any combination of steps 820, 830, 840, and 850 can be used in an embodiment of the present disclosure, as readily contemplated by one skilled in the art.

Interactive Test Application for Outputting a Screening Result

Figure 9:
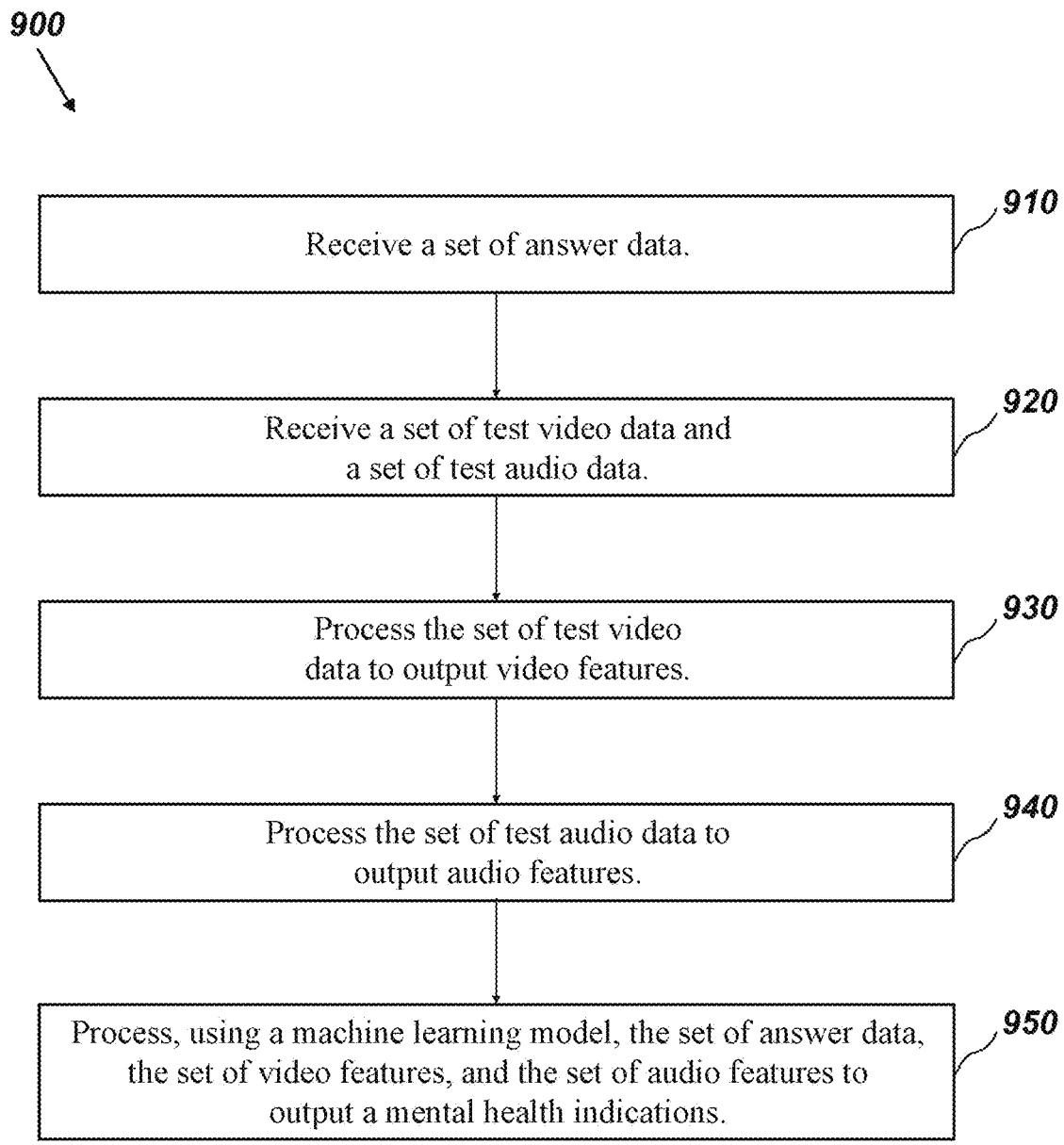
FIG. 9 shows an exemplary methodology for analyzing input with a machine learning model, according to an embodiment of the present disclosure.

FIG. 9 shows an exemplary methodology 900, according to an exemplary implementation of the present disclosure. Methodology 900 provides a method of administering a test to a user and can be provided for by the system 700A, as discussed above with respect to FIG. 7A.

Methodology 900 provides for, at step 910, receiving a set of answer data. In some examples, the answer data includes answers from a user to a series of questions from mental health questionnaires.

Methodology 900 then provides for, at step 920, receiving a set of test video data and test audio data. In some examples, the test video data and test audio data is recorded by a camera and a microphone (e.g., camera 706 and microphone 712 of FIG. 7A). The test video data is recorded during a test (e.g., the tests of methodologies 700B and 800 of FIGS. 7B and 8) and includes the face of the user, while the user is reading text. For example, the text is displayed according to methodology 800 of FIG. 8. The set of test audio data is also recorded during the test and represents the voice of the user, while the user is reading the text.

Step 930 of methodology 900 then provides for processing the set of test video data to output video features. Step 940 provides for processing the set of test audio data to output audio features. In some examples, steps 930-940 are performed according to method 730 of FIG. 7C.

Methodology 900 further provides for, at step 950, processing the set of answer data, the set of video features, and the set of audio features to output a mental health indication. In some examples, step 950 is performed as discussed above with respect to methodology 740 of FIG. 7D.

Machine Learning Implementation

Various aspects of the present disclosure can be performed by a machine-learning algorithm, as readily understood by a person skilled in the art. In some examples, step 725 of FIG. 7B, methodology 740, step 850 of FIG. 8 and step 950 of FIG. 9 can be performed by a supervised or unsupervised algorithm. For instance, the system may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms, e.g., convolutional neural networks ("CNN"), or capsule networks ("CapsNet") may be used.

DT are classification graphs that match input data to questions asked at each consecutive step in a decision tree. The DT program moves down the "branches" of the tree based on the answers to the questions (e.g., First branch: Did the user pause before reading the question? yes or no. Branch two: Did the user stutter while reading the question? yes or no, etc.).

Bayesian networks ("BN") are based on likelihood something is true based on given independent variables and are modeled based on probabilistic relationships. BN are based purely on probabilistic relationships that determine the likelihood of one variable based on another or others. For example, BN can model the relationships between location data, time stamp data, previous alerts, and any other information as contemplated by the present disclosure. Particularly, if a question type and particular features of the user's auditory data are known, a BN can be used to compute the probability that a user has a particular mental health disorder. Thus, using an efficient BN algorithm, an inference can be made based on the input data.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer. ANNs are capable of pattern recognition. Their computing methods make it easier to understand a complex and unclear process that might go on during predicting a mental health disorder based a variety of input data.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

Deep neural networks (DNN) have developed recently and are capable of modeling very complex relationships that have a lot of variation. Various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory) etc. They are all based on the theory of ANN. They demonstrate a better performance by overcoming the back-propagation error diminishing problem associated with ANN.

Machine learning models require training data to identify the features of interest that they are designed to detect. For instance, various methods may be utilized to form the machine learning models, including applying randomly assigned initial weights for the network and applying gradient descent using back propagation for deep learning algorithms. In other examples, a neural network with one or two hidden layers can be used without training using this technique.

In some examples, the machine learning model can be trained using labeled data, or data that represents certain user input. In other examples, the data will only be labeled with the outcome and the various relevant data may be input to train the machine learning algorithm.

For instance, to determine whether particular mental health disorder fits the input data, various machine learning models may be utilized that input various data disclosed herein. In some examples, the input data will be labeled by having an expert in the field label the relevant regulations according to the particular situation. Accordingly, the input to the machine learning algorithm for training data identifies various data as from a healthy control or from a patient.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

Kessler R C, et al. *Short screening scales to monitor population prevalences and trends in non-specific psychological distress*. Psychological Medicine 32:959-976 (2002)
Kessler R C, et al. *Screening for serious mental illness in the general population*. Arch Gen Psychiatry 60:184-189 (2003)
Kessler R C, et al. *The WHO World Mental Health (WMH) Surveys*. Psychiatrie (Stuttg) 6 (1):5-9 (2009).
White P D, Rickards H, Zeman A Z J. *Time to end the distinction between mental and neurological illnesses*. BMJ 344:e3454 (2012).

What is claimed is:

1. A system for evaluating a user, the system comprising:
a microphone;
a camera positioned to capture an image of the user and configured to output video data;
a memory containing machine readable medium comprising machine executable code having stored thereon instructions for performing a method of evaluating the user; and
a control system coupled to the memory comprising one or more processors, the control system configured to execute the machine executable code to cause the control system to:
record, by the camera, a set of test video data during a time period;
record, by the microphone, a set of test audio data during the time period;
process the video data to assign a plurality of pixels to a face of the user;
analyze the plurality of pixels to determine whether the face of the user is within a frame captured by the camera;
in response to determining that the face of the user is within the frame captured by the camera, process the plurality of pixels to output video features associated with the user;
process the audio data to identify sounds representing a voice of the user and output audio features associated with the user;
process, using a machine learning model, the audio and video features, wherein the machine learning model was previously trained with a set of training data comprising audio and video data recorded from a plurality of individuals with labels indicating whether each of the plurality of individuals has one of a plurality of characteristics; and
output an indication of whether the user has at least one of the plurality of characteristics.

2. The system of claim 1, wherein the processing the audio data to identify sounds is in response to determining that the face of the user is within the frame captured by the camera during the time period.

3. The system of claim 1, wherein the analyzing the plurality of pixels includes determining whether an entire face of the user is within the frame captured by the camera, and wherein the processing the plurality of pixels is in response to determining that the entire face of the user is within the frame captured by the camera.

4. The system of claim 3, wherein the plurality of pixels is assigned to a boundary of the face of the user, and wherein the determining whether the entire face of the user is within the frame captured by the camera includes determining whether the boundary of the face of the user is within the frame captured by the camera.

5. The system of claim 3, wherein the determining whether the entire face of the user is within the frame captured by the camera includes determining whether all of the plurality of pixels of the face of the user is within the frame captured by the camera.

6. The system of claim 1, wherein the video features include facial expressions of the user.

7. The system of claim 1, wherein the audio features include tone of voice of the user.

8. The system of claim 1, wherein the recording, by the microphone, further includes initiating the recording upon determining, by the control system, that the user is speaking.

9. The system of claim 1, wherein the control system is further caused to:
preprocess the recorded set of test video data to identify a plurality of video segments during the time period, each video segment corresponding to one question in a series of questions and comprising a time window; and
preprocess the recorded set of test audio data to identify a plurality of audio segments during the time period, each audio segment corresponding to one question in the series of questions and comprising a time window.

10. The system of claim 9, wherein the control system is further caused to:
preprocess the plurality of audio segments and the plurality of video segments to identify overlapping time windows; and output a set of integrated audio and video segments based on the identified overlapping time windows.

11. The system of claim 10, wherein only the audio and video features associated with the set of integrated audio and video segments are processed using the machine learning model.

12. The system of claim 1, wherein the time period corresponds to the user reading a text.

13. The system of claim 12, further comprising a display configured to be placed in front of the user and displaying the text, such that the camera is positioned to capture the image of the user in front of the display.

14. The system of claim 12, wherein the text includes a series of questions from questionnaires answers for each question, and wherein the questionnaires are associated with the plurality of characteristics.

15. The system of claim 14, wherein each of the plurality of characteristics is indicative of a mental health disorder.

16. The system of claim 1, wherein the machine learning model is at least one of: a generalized linear model, a regression model, a logistical regression model, and a supervised machine learning classification model.

17. The system of claim 16, wherein the machine learning model includes a decision tree.

18. A system for screening mental health of a user, the system comprising:
a memory containing machine readable medium comprising machine executable code having stored thereon instructions for performing a method; and
a control system coupled to the memory comprising one or more processors, the control system configured to execute the machine executable code to cause the control system to:
receive a set of test video data representing a face of the user while the user is reading text;
process the set of test video data to output a set of video features associated with the face of the user;
receive a set of test audio data representing a voice of the user while the user is reading the text;
identify sounds representing the voice of the user;
process the set of test audio data to output a set of audio features based at least in part on the identified sounds presenting the voice of the user;
process, using a machine learning model, the set of video features and the set of audio features, to output an indication of the mental health of the user,
wherein the machine learning model is at least one of: a generalized linear model, a regression model, a logistical regression model, and a supervised machine learning classification model, and
wherein the machine learning model was previously trained with a set of training data comprising audio and video data recorded from a plurality of individuals with labels indicating whether each of the plurality of individuals has one of a plurality of mental health disorders; and
output an indication of whether the user has a mental health disorder.

19. The system of claim 18, wherein the control system is further caused to determine whether the face of the user is within the set of test video data, and wherein the set of test video data is processed in response to determining that the face of the user is within the set of test video data.

20. The system of claim 19, wherein the set of test video data is generated by a camera, and wherein the determining whether the face of the user is within the set of test video data includes determining whether all of a plurality of pixels of the face of the user is within a frame captured by the camera.

21. The system of claim 19, wherein the set of test video data is generated by a camera, and wherein the determining whether the face of the user is within the set of test video data includes determining whether all of a plurality of pixels assigned to a boundary of the face of the user is within a frame captured by the camera.

* * * * *